United States Patent
Andree et al.

(10) Patent No.: US 6,602,826 B1
(45) Date of Patent: Aug. 5, 2003

(54) HETEROCYCLICALLY SUBSTITUTED AROMATIC AMINO COMPOUNDS WITH A HERBICIDAL EFFECT

(75) Inventors: Roland Andree, Langenfeld (DE); Mark Wilhelm Drewes, Langenfeld (DE); Kurt Findeisen, Leverkusen (DE); Joachim Kluth, Langenfeld (DE); Karl-Heinz Linker, Leverkusen (DE); Klaus-Helmut Müller, Düsseldorf (DE); Otto Schallner, Monheim (DE); Markus Dollinger, Overland Park, KS (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/367,476

(22) PCT Filed: Feb. 20, 1998

(86) PCT No.: PCT/EP98/00972

§ 371 (c)(1),
(2), (4) Date: Sep. 20, 1999

(87) PCT Pub. No.: WO98/39304

PCT Pub. Date: Sep. 11, 1998

(30) Foreign Application Priority Data

Mar. 5, 1997 (DE) .......................................... 197 08 928

(51) Int. Cl.⁷ .................... A01N 43/54; C07D 239/553; C07D 239/545; C07D 239/54
(52) U.S. Cl. ...................... 504/243; 544/311; 544/312
(58) Field of Search ................. 544/311, 312; 504/243

(56) References Cited

U.S. PATENT DOCUMENTS 3,489,761 A    1/1970  Kauer ........................ 260/296
4,138,404 A    2/1979  Fort et al. ................ 260/307 A
4,496,390 A    1/1985  Hatton et al. .................... 71/92
4,629,495 A    12/1986 Hatton et al. .................... 71/92
5,084,084 A  * 1/1992  Satow et al. .................... 71/92
5,356,863 A    10/1994 Satow et al. ................. 504/243
6,355,799 B1 * 3/2002  Gupta et al. ................. 544/309

FOREIGN PATENT DOCUMENTS

CA        2119673         9/1994
WO    WO 94/04511    *   3/1994
WO    WO 96/07323    *   3/1995

OTHER PUBLICATIONS

Indian Journal of Chem., vol. 29B, Jul., 1990, pp. 659–660, Balasubramaniyan et al, "Synthesis of azamitosane congeners: 3a–Acetoxy–4–acetyl–3a, 4–dihydro–1H–pyrrolo[1,2–a]benzimidazol–1–ones".

* cited by examiner

Primary Examiner—Patricia L. Morris
(74) Attorney, Agent, or Firm—Richard E. L. Henderson; John E. Mrozinski, Jr.

(57) ABSTRACT

The invention relates to new substituted aromatic amino compounds of the general formula (I)

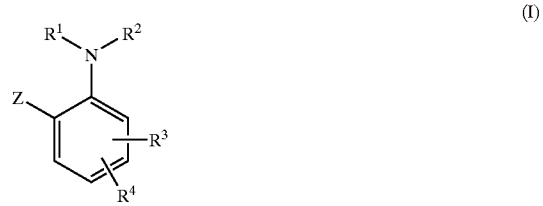

in which
$R^1$, $R^2$, $R^3$, $R^4$ and Z have the meanings given in the description, to a process for their preparation, and to their use as herbicides.

4 Claims, No Drawings

HETEROCYCLICALLY SUBSTITUTED AROMATIC AMINO COMPOUNDS WITH A HERBICIDAL EFFECT

This application is a 317 of PCT/EP98/00972 filed Feb. 20, 1998.

TECHNICAL FIELD OF THE INVENTION

The invention relates to new substituted aromatic amino compounds, the processes for their preparation, and to their use as herbicides.

BACKGROUND OF THE INVENTION

Some substituted aromatic amino compounds such as, for example, N-[2-(1,5-dihydro-1-methyl-5-thioxo-3-trifluoromethyl-4H-1,2,4-triazol-4-yl)-5-fluorophen-yl]-benzamide and N-[5-chloro-2-(1,5-dihydro-1-methyl-5-thioxo-3-trifluoromethyl-4H-1,2,4-triazol-4-yl)-phenyl]-acetamide have already been disclosed in the patent literature as candidate herbicides (cf. U.S. Pat. No. 5,108,486). However, these compounds have not gained any particular importance.

Other substituted aromatic amino compounds such as, for example, N-[5-chloro-2-(2,5-dihydro-3,4-dimethyl-2,5-dioxo-1H-pyrrol-1-yl)-phenyl]-acetamide (cf. Indian J. Chem, Sect. B, 29B (1990), 659–660—cited in Chem. Abstracts 113:211906) and N-[2-(5-diethylamino-3-t-butyl-1H-1,2,4-triazol-1-yl)-5-trifluoromethyl-phenyl]-2,2-dimethyl-propanamide and N-[2-(5-diethylamino-3-t-butyl-1H-1,2,4-triazol-1-yl)-5-trifluoromethyl-phenyl]-acetamide (cf. JP 02091062—cited in Chem. Abstracts 113:97612) are also known already. However, nothing has been disclosed about the herbicidal activity of these compounds.

DETAILED DESCRIPTION OF THE INVENTION

There have now been found new substituted aromatic amino compounds of the general formula (I)

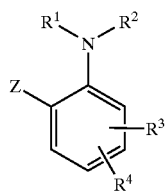

(I)

in which $R^1$ represents hydrogen, hydroxyl, amino, alkyl, alkoxy, alkylamino or dialkylamino, or represents one of the groups which follow,

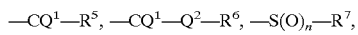

$R^2$ represents one of the groups which follow,

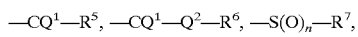

$R^3$ represents hydrogen, hydroxyl, amino, carboxyl, cyano, carbamoyl, thiocarbamoyl, nitro, halogen, in each case optionally substituted alkyl, alkoxy, alkoxycarbonyl, alkylthio, alkylsulphinyl or alkylsulphonyl, or one of the groups which follow,

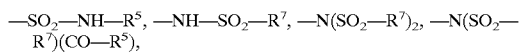

$R^4$ represents hydrogen, hydroxyl, amino, carboxyl, cyano, carbamoyl, thiocarbamoyl, nitro, halogen, in each case optionally substituted alkyl, alkoxy, alkoxycarbonyl, alkylthio, alkylsulphinyl or alkylsulphonyl, or one of the groups which follow,

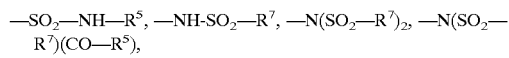

n represents the numbers 0, 1 or 2, $Q^1$ represents O or S and $Q^2$ represents O, S, NH or N-alkyl, $R^5$ represents hydrogen or in each case optionally substituted alkyl, cycloalkyl, cycloalkylalkyl, aryl, arylalkyl or heterocyclyl, $R^6$ represents in each case optionally substituted alkyl, alkenyl, alkinyl, cycloalkyl, cycloalkylalkyl, aryl or arylalkyl, $R^7$ represents in each case optionally substituted alkyl, cycloalkyl, cycloalkylalkyl, aryl, arylalkyl or heterocyclyl, and Z represents one of the heterocyclic groups which follow

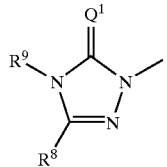
(Z¹)

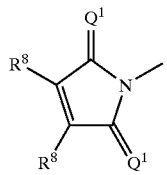
(Z²)

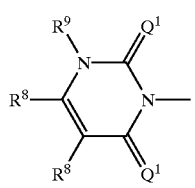
(Z³)

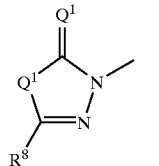
(Z⁴)

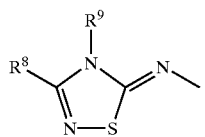
(Z⁵)

-continued
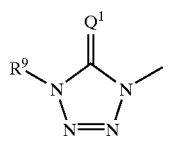 (Z⁶)
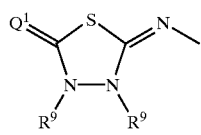 (Z⁷)
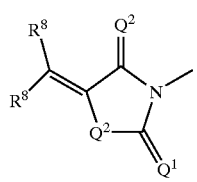 (Z⁸)
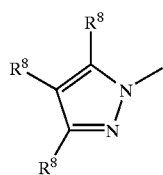 (Z⁹)
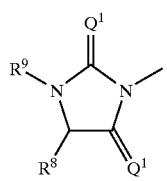 (Z¹⁰)
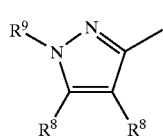 (Z¹¹)
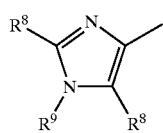 (Z¹²)
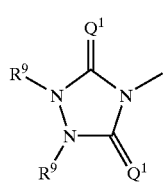 (Z¹³)
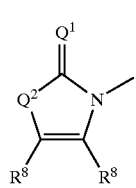 (Z¹⁴)
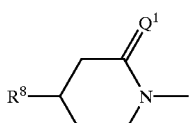 (Z¹⁵)
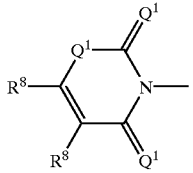 (Z¹⁶)
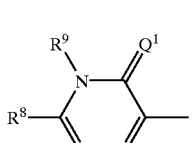 (Z¹⁷)
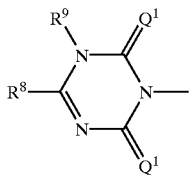 (Z¹⁸)
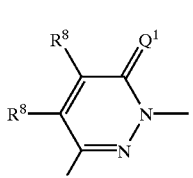 (Z¹⁹)
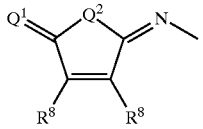 (Z²⁰)
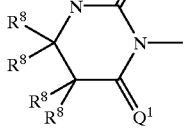 (Z²¹)
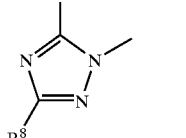 (Z²²)
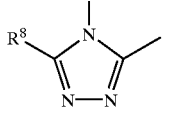 (Z²³)

-continued

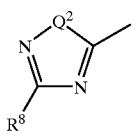 (Z²⁴)

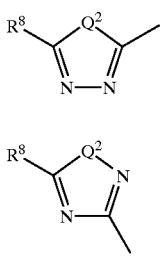 (Z²⁵)

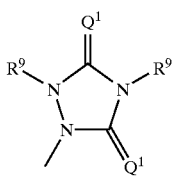 (Z²⁶)

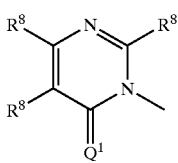 (Z²⁷)

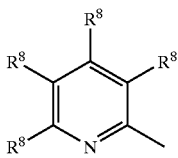 (Z²⁸)

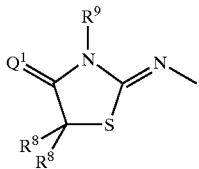 (Z²⁹)

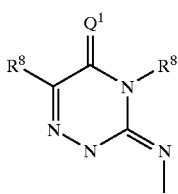 (Z³⁰)

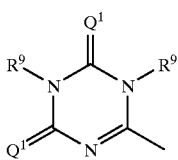 (Z³¹)

-continued

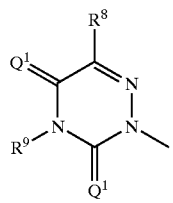 (Z³³)

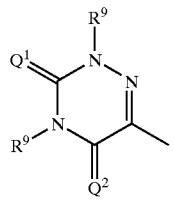 (Z³⁴)

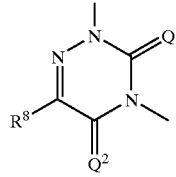 (Z³⁵)

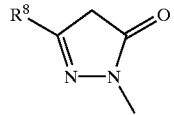 (Z³²)

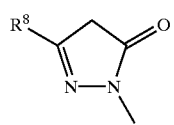 (Z³⁶)

where in each case $Q^1$ and $Q^2$ have the abovementioned meaning, $R^8$ represents hydrogen, amino, nitro, cyano, carboxyl, carbamoyl, thiocarbamoyl, halogen, or in each case optionally substituted alkyl, alkenyl, alkinyl, alkoxy, alkoxycarbonyl, alkenyloxy, alkinyloxy, alkylthio, alkenylthio, alkinylthio, alkylamino, dialkylamino, cycloalkyl or cycloalkylalkyl, and $R^9$ represents hydrogen, hydroxyl, amino, cyano, or in each case optionally substituted alkyl, alkenyl, alkinyl, alkoxycarbonyl, cycloalkyl, cycloalkylalkyl, phenyl or phenylalkyl, where, if appropriate, two adjacent radicals—$R^8$ and $R^8$, $R^9$ and $R^9$ or $R^8$ and $R^9$—together represent alkanediyl (alkylene) or oxaalkanediyl, and where the individual radicals $R^8$ and $R^9$—if they occur more than once in the same heterocyclic group, may have identical or different meanings within the scope of the above definition, with the exception of the prior-art compound N-[5-chloro-2-(2,5-dihydro-3,4-dimethyl-2,5-dioxo-1H-pyrrol-1-yl)-phenyl]-acetamide (cf. Indian J. Chem, Sect. B, 29B (1990), 659–660—cited in Chem. Abstracts 113:211906), and of N-[2-(5-diethylamino-3-t-butyl-1H-1,2,4-triazol-1-yl)-5-trifluoromethyl-pheny]-2,2-dimethyl-propanamide and N-[2-(5-diethylamino-3-t-butyl-1H-1,2,4-triazol-1-yl)-5-trifluoromethyl-phenyl]-acetamide (cf. JP 02091062—cited in Chem. Abstracts 113:97612), which are also prior-art compounds.

The new substituted aromatic amino compounds of the general formula (I) are obtained when aromatic amino compounds of the general formula (II)

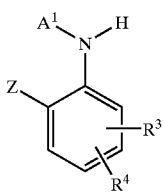 (II)

in which
R³, R⁴ and Z have the abovementioned meaning and
A¹ represents hydrogen, hydroxyl, amino, alkyl, alkoxy, alkylamino or dialkylamino
are reacted with electrophilic compounds of the general formula (III)

X—R² (III)

in which
R² has the abovementioned meaning and
X represents halogen,
if appropriate in the presence of an acid acceptor and if appropriate in the presence of a diluent,
and the resulting compounds of the general formula (I) are converted into other compounds of the general formula (I) in accordance with the above definition (cf. the preparation examples), if appropriate by customary methods.

The new substituted aromatic amino compounds of the general formula are distinguished by a potent and selective herbicidal activity.

In the definitions, the saturated or unsaturated hydrocarbon chains, such as alkyl, alkanediyl, alkenyl or alkinyl—also in connection with hetero atoms, such as in alkoxy, alkylthio or alkylamino—are in each case straight-chain or branched.

Halogen generally represents fluorine, chlorine, bromine or iodine, preferably fluorine, chlorine or bromine, in particular fluorine or chlorine.

The invention preferably relates to compounds of the formula (I)
in which
R¹ represents hydrogen, hydroxyl, amino, or represents alkyl, alkoxy, alkylamino or dialkylamino, each of which has 1 to 6 carbon atoms in the alkyl groups, or represents one of the groups which follow, —CQ¹—R⁵, —CQ¹—Q²—R⁶, —S(O)$_n$—R⁷, R² represents one of the groups which follow, —CQ¹—R⁵, —CQ¹—Q²—R⁶, —S(O)$_n$—R⁷, R³ represents hydrogen, hydroxyl, amino, carboxyl, cyano, carbamoyl, thiocarbamoyl, nitro, halogen, or represents alkyl, alkoxy, alkoxycarbonyl, alkylthio, alkylsulphinyl or alkylsulphonyl, each of which has 1 to 6 carbon atoms in the alkyl groups and each of which is optionally substituted by cyano, halogen or C₁–C₄-alkoxy, or represents one of the groups which follow,

—SO₂—NH—R⁵, —NH—SO₂—R⁷, —N(SO₂—R⁷)₂, —N(SO₂—R⁷)(CO—R⁵),

R⁴ represents hydrogen, hydroxyl, amino, carboxyl, cyano, carbamoyl, thiocarbamoyl, nitro, halogen, or represents alkyl, alkoxy, alkoxycarbonyl, alkylthio, alkylsulphinyl or alkylsulphonyl, each of which has 1 to 6 carbon atoms in the alkyl groups and each of which is optionally substitued by cyano, halogen or C₁–C₄-alkoxy, or represents one of the groups which follow,

—SO₂—NH—R⁵, —NH—SO₂—R⁷, —N(SO₂—R⁷)₂, —N(SO₂—R⁷)(CO—R⁵), n represents the numbers 0, 1 or 2,
Q¹ represents O or S and
Q² represents O, S, NH or N-alkyl having 1 to 4 carbon atoms,
R⁵ represents hydrogen, or represents alkyl which has 1 to 6 carbon atoms and which is optionally substituted by cyano, halogen or C₁–C₄-alkoxy, or represents cycloalkyl or cycloalkylalkyl, each of which has 3 to 6 carbon atoms in the cycloalkyl group and, if appropriate, 1 to 4 carbon atoms in the alkyl moiety and each of which is optionally substituted by cyano, halogen or C₁–C₄-alkyl, or represents aryl or arylalkyl, each of which has 6 or 10 carbon atoms in the aryl group and, where appropriate, 1 to 4 carbon atoms in the alkyl moiety and each of which is optionally substituted by cyano, nitro, halogen, C₁–C₄-alkyl, C₁–C₄-halogenoalkyl, C₁–C₄-alkoxy or C₁–C₄-halogenoalkoxy, or represents heterocyclyl which is optionally substituted by halogen, C₁–C₄-alkyl, C₁–C₄-halogenoalkyl, C₁–C₄-alkoxy or C₁–C₄-halogenoalkoxy, preferred heterocyclyl groups being furyl, tetrahydrofuryl, thienyl, pyridyl and pyrimidinyl,
R⁶ represents alkyl which has 1 to 6 carbon atoms and which is optionally substituted by cyano, halogen or C₁–C₄-alkoxy, or represents alkenyl or alkinyl, each of which has 2 to 6 carbon atoms and each of which is optionally substituted by halogen, or represents cycloalkyl or cycloalkylalkyl, each of which has 3 to 6 carbon atoms in the cycloalkyl group and, if appropriate, 1 to 4 carbon atoms in the alkyl moiety and each of which is optionally substituted by cyano, halogen or C₁–C₄-alkyl, or represents aryl or arylalkyl, each of which has 6 or 10 carbon atoms in the aryl group and, if appropriate, 1 to 4 carbon atoms in the alkyl moiety and each of which is optionally substituted by cyano, nitro, halogen, C₁–C₄-alkyl, C₁–C₄-halogenoalkyl, C₁–C₄-alkoxy or C₁–C₄-halogenoalkoxy,
R⁷ represents alkyl which has 1 to 6 carbon atoms and which is optionally subsituted by halogen, or represents cycloalkyl or cycloalkylalkyl, each of which has 3 to 6 carbon atoms in the cycloalkyl moiety and, if appropriate, 1 to 4 carbon atoms in the alkyl moiety and each of which is optionally substituted by halogen, or represents aryl or arylalkyl, each of which has 6 or 10 carbon atoms in the aryl group and, if appropriate, 1 to 4 carbon atoms in the alkyl moiety and each of which is optionally substituted by cyano, nitro, halogen, C₁–C₄-alkyl, C₁–C₄-halogenoalkyl, C₁–C₄-alkoxy, C₁–C₄-halogenoalkoxy, C₁–C₄-alkylthio, C₁–C₄-alkylsulphinyl, C₁–C₄-alkylsulphonyl or C₁–C₄-alkoxy-carbonyl, or represents heterocyclyi which is optionally substituted by halogen, C₁–C₄-alkyl, C₁–C₄-halogenoalkyl, C₁–C₄-alkoxy or C₁–C₄-halogenoalkoxy, preferred heterocyclyl groups being pyridyl and pyrimidinyl, and Z represents one of the heterocyclic groups which follow
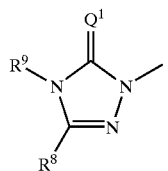 (Z¹)
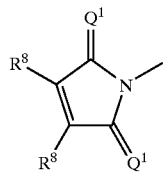 (Z²)
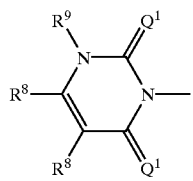 (Z³)
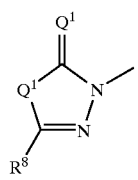 (Z⁴)
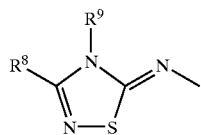 (Z⁵)
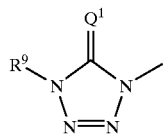 (Z⁶)
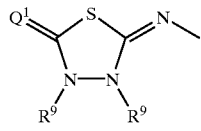 (Z⁷)
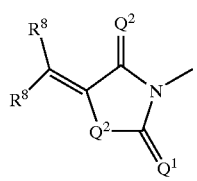 (Z⁸)
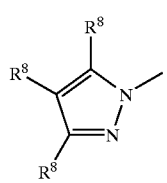 (Z⁹)
-continued
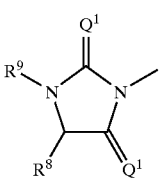 (Z¹⁰)
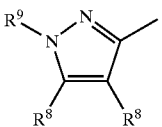 (Z¹¹)
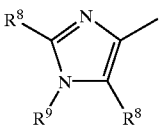 (Z¹²)
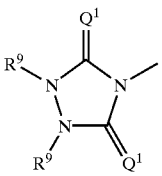 (Z¹³)
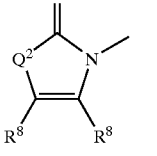 (Z¹⁴)
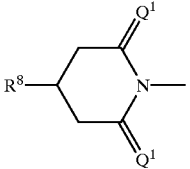 (Z¹⁵)
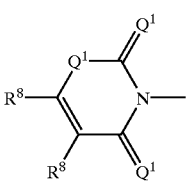 (Z¹⁶)
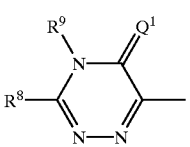 (Z¹⁷)
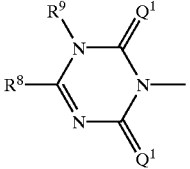 (Z¹⁸)

-continued
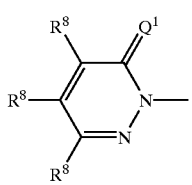 (Z19)
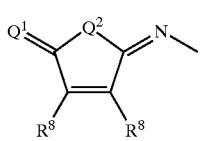 (Z20)
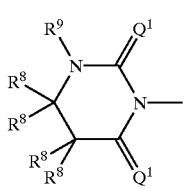 (Z21)
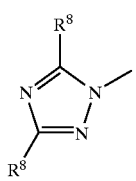 (Z22)
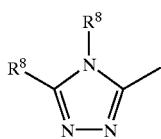 (Z23)
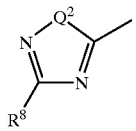 (Z24)
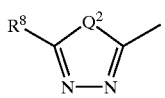 (Z25)
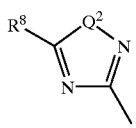 (Z26)
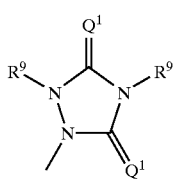 (Z27)
-continued
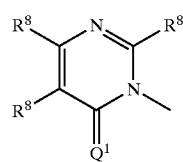 (Z28)
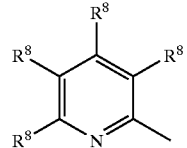 (Z29)
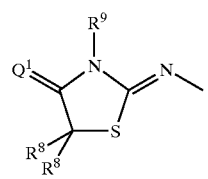 (Z30)
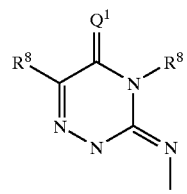 (Z31)
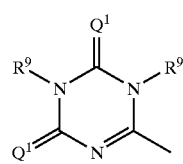 (Z32)
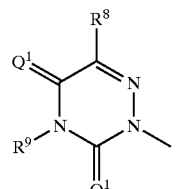 (Z33)
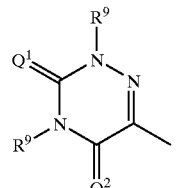 (Z34)
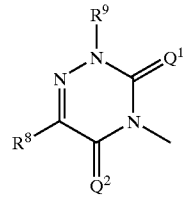 (Z35)

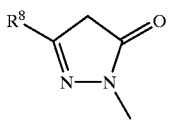
(Z$^{36}$)

where in each case

Q$^1$ and Q$^2$ have the abovementioned meaning,

R$^8$ represents hydrogen, amino, nitro, cyano, carboxyl, carbamoyl, thiocarbamoyl, halogen, or represents alkyl which has 1 to 6 carbon atoms and which is optionally substituted by cyano, halogen or C$_1$–C$_4$-alkoxy, or represents alkenyl or alkinyl, each of which has 2 to 6 carbon atoms and each of which is optionally substituted by halogen, or represents alkoxy or alkoxycarbonyl, each of which has 1 to 6 carbon atoms in the alkyl groups and each of which is optionally substituted by cyano, halogen or C$_1$–C$_4$-alkoxy, or represents alkenyloxy or alkinyloxy, each of which has 3 to 6 carbon atoms and each of which is optionally substituted by halogen, or represents alkylthio which has 1 to 6 carbon atoms and which is optionally substituted by cyano, halogen or C$_1$–C$_4$-alkoxy, or represents alkenylthio or alkinylthio, each of which has 3 to 6 carbon atoms and each of which is optionally substituted by halogen, or represents alkylamino or dialkylamino, each of which has 1 to 6 carbon atoms in the alkyl groups each of which is optionally substituted by cyano, halogen or C$_1$–C$_4$-alkoxy, or represents cycloalkyl or cycloalkylalkyl, each of which has 3 to 6 carbon atoms in the cycloalkyl groups and, if appropriate, 1 to 4 carbon atoms in the alkyl moiety and each of which is optionally substituted by cyano, halogen or C$_1$–C$_4$-alkyl, and R$^9$ represents hydrogen, hydroxyl, amino, cyano, or represents alkyl which has 1 to 6 carbon atoms and which is optionally substituted by cyano, halogen or C$_1$–C$_4$-alkoxy, or represents alkenyl or alkinyl, each of which has 2 to 6 carbon atoms and which is optionally substituted by halogen, or represents alkoxycarbonyl, which is optionally substituted by cyano, halogen or C$_1$–C$_4$-alkoxy, or represents cycloalkyl or cycloalkylalkyl, each of which has 3 to 6 carbon atoms in the cycloalkyl groups and, if appropriate, 1 to 4 carbon atoms in the alkyl moiety and each of which is optionally substituted by cyano, halogen or C$_1$–C$_4$-alkyl, or represents phenyl or phenyl-C$_1$–C$_4$-alkyl, each of which is optionally substituted by cyano, nitro, halogen, C$_1$–C$_4$-alkyl, C$_1$–C$_4$-halogenoalkyl, C$_1$–C$_4$-alkoxy and/or C$_1$–C$_4$-halogenoalkoxy, where, if appropriate, two adjacent radicals—R$^8$ and R$^8$, R$^9$ and R$^9$ or R$^8$ and R$^9$—together represent alkanediyl (alkylene) or oxaalkanediyl having in each case 2 to 6 carbon atoms, and where the individual radicals R$^8$ and R$^9$—if they occur more than once in the same heterocyclic group, may have identical or different meanings within the above definition, with the exception of the prior-art compound N-[5-chloro-2-(2,5-dihydro-3,4-dimethyl-2,5-dioxo-1H-pyrrol-1-yl)-phenyl]-acetamide (cf. Indian J. Chem, Sect. B, 29B (1990), 659–660—cited in Chem. Abstracts 113:211906), and of N-[2-(5-diethylamino-3-t-butyl-1H-1,2,4-triazol-1-yl)-5-trifluoromethyl-phenyl]-2,2-dimethyl-propanamide and N-[2-(5-diethylamino-3-t-butyl-1H-1,2,4-triazol-1-yl)-5-trifluoromethyl-phenyl]-acetamide (cf. JP 02091062—cited in Chem. Abstracts 113:97612), which are also prior-art compounds.

The invention particularly relates to compounds of the formula (I) in which

R$^1$ represents hydrogen, hydroxyl, amino, methyl, ethyl, n- or i-propyl, n-, i-, s- or t-butyl, methoxy, ethoxy, n- or i-propoxy, n-, i-, s- or t-butoxy, methylamino, ethylamino, n- or i-propylamino, n-, i-, s- or t-butylamino or dimethylamino, or one of the groups which follow,

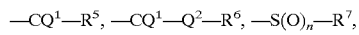
—CQ$^1$—R$^5$, —CQ$^1$—Q$^2$—R$^6$, —S(O)$_n$—R$^7$,

R$^2$ represents one of the groups which follow,

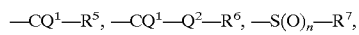
—CQ$^1$—R$^5$, —CQ$^1$—Q$^2$—R$^6$, —S(O)$_n$—R$^7$,

R$^3$ represents hydrogen, hydroxyl, amino, carboxyl, cyano, carbamoyl, thiocarbamoyl, nitro, fluorine, chlorine, bromine, or represents methyl, ethyl, n- or i-propyl, n-, i-, s- or t-butyl, methoxy, ethoxy, n- or i-propoxy, n-, i-, s- or t-butoxy, methoxycarbonyl, ethoxycarbonyl, methylthio, ethylthio, n- or i-propylthio, n-, i-, s- or t-butylthio, methylsulphinyl, ethylsulphinyl, methylsulphonyl or ethylsulphonyl, each of which is optionally substituted by cyano, fluorine, chlorine, methoxy or ethoxy, or represents one of the groups which follow,

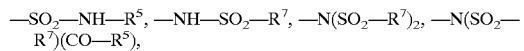
—SO$_2$—NH—R$^5$, —NH—SO$_2$—R$^7$, —N(SO$_2$—R$^7$)$_2$, —N(SO$_2$—R$^7$)(CO—R$^5$), R$^4$ represents hydrogen, hydroxyl, amino, carboxyl, cyano, carbamoyl, thiocarbamoyl, nitro, fluorine, chlorine, bromine, or represents methyl, ethyl, n- or i-propyl, n-, i-, s- or t-butyl, methoxy, ethoxy, n- or i-propoxy, n-, i-, s- or t-butoxy, methoxycarbonyl, ethoxycarbonyl, methylthio, ethylthio, n- or i-propylthio, n-, i-, s- or t-butylthio, methylsulphinyl, ethylsulphinyl, methylsulphonyl or ethylsulphonyl, each of which is optionally substituted by cyano, fluorine, chlorine, methoxy or ethoxy, or represents one of the groups which follow,

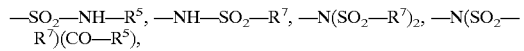
—SO$_2$—NH—R$^5$, —NH—SO$_2$—R$^7$, —N(SO$_2$—R$^7$)$_2$, —N(SO$_2$—R$^7$)(CO—R$^5$), n represents the numbers 0, 1 or 2, Q$^1$ represents O or S and Q$^2$ represents O, S, NH or N-methyl, R$^5$ represents hydrogen, or represents methyl, ethyl, n- or i-propyl, n-, i-, s- or t-butyl, each of which is optionally substituted by cyano, fluorine, chlorine, bromine, methoxy or ethoxy, or represents cyclopropyl, cyclobutyl, cyclopentyl, cyclohexyl, cyclopropylmethyl, cyclobutylmethyl, cyclopentylmethyl or cyclohexylmethyl, each of which is optionally substituted by cyano, fluorine, chlorine, bromine, methyl or ethyl, or represents phenyl or benzyl, each of which is optionally substituted by cyano, nitro, fluorine, chlorine, bromine, methyl, ethyl, n- or i-propyl, n-, i-, s- or t-butyl, trifluoromethyl, methoxy, ethoxy, n- or i-propoxy, n-, i-, s- or t-butoxy, difluoromethoxy or trifluoromethoxy, or represents furyl, tetrahydrofuryl, thienyl or pyridyl, each of which is optionally substituted by fluorine, chlorine, bromine, methyl, ethyl, n- or i-propyl, n-, i-, s- or t-butyl, trifluoromethyl, methoxy, ethoxy, n- or i-propoxy, n-, i-, s- or t-butoxy, difluoromethoxy or trifluoromethoxy, $R^6$ represents methyl, ethyl, n- or i-propyl, n-, i-, s- or t-butyl, each of which is optionally substituted by cyano, fluorine, chlorine, methoxy or ethoxy, or represents propenyl, butenyl, propinyl or butinyl, each of which is optionally substituted by fluorine, chlorine or bromine, or represents cyclopropyl, cyclobutyl, cyclopentyl, cyclohexyl, cyclopropylmethyl, cyclobutylmethyl, cyclopentylmethyl or cyclohexylmethyl, each of which is optionally substituted by cyano, fluorine, chlorine, bromine, methyl or ethyl, or represents phenyl or benzyl, each of which is optionally substituted by cyano, nitro, fluorine, chlorine, bromine, methyl, ethyl, n- or i-propyl, n-, i-, s- or t-butyl, trifluoromethyl, methoxy, ethoxy, n- or i-propoxy, n-, i-, s- or t-butoxy, difluoromethoxy or trifluoromethoxy, $R^7$ represents methyl, ethyl, n- or i-propyl, n-, i-, s- or t-butyl, each of which is optionally substituted by fluorine, chlorine or bromine, or represents cyclopropyl, cyclobutyl, cyclopentyl, cyclohexyl, cyclopropylmethyl, cyclobutylmethyl, cyclopentylmethyl or cyclohexylmethyl, each of which is optionally substituted by fluorine, chlorine or bromine, or represents phenyl or benzyl, each of which is optionally substituted by cyano, nitro, fluorine, chlorine, bromine, methyl, ethyl, n- or i-propyl, n-, i-, s- or t-butyl, trifluoromethyl, methoxy, ethoxy, n- or i-propoxy, n-, i-, s- or t-butoxy, difluoromethoxy, trifluoromethoxy, methylthio, ethylthio, n- or i-propylthio, n-, i-, s- or t-butylthio, methylsulphinyl, ethylsulphinyl, methylsulphonyl, ethylsulphonyl, methoxycarbonyl or ethoxy-carbonyl or represents pyridyl or pyrimidinyl, each of which is optionally substituted by fluorine, chlorine, bromine, methyl, ethyl, n- or i-propyl, n-, i-, s- or t-butyl, trifluoromethyl, methoxy, ethoxy, n- or i-propoxy, n-, i-, s- or t-butoxy, difluoromethoxy, and Z represents one of the heterocyclic groups which follow

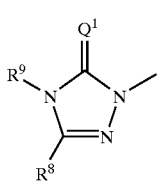 (Z¹)

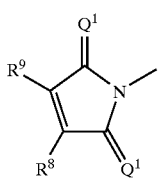 (Z²)

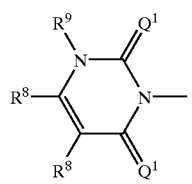 (Z³)

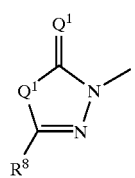 (Z⁴)

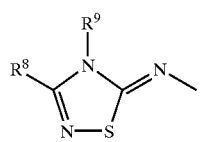 (Z⁵)

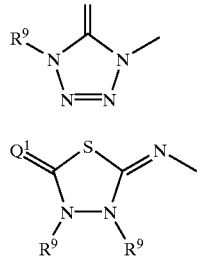 (Z⁶)

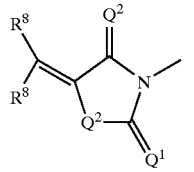 (Z⁷)

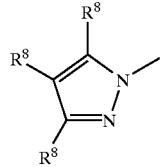 (Z⁸)

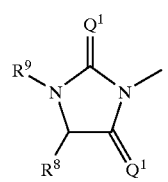 (Z⁹)

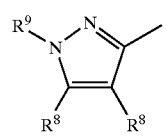 (Z¹⁰)

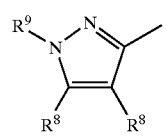 (Z¹¹)

(Z¹²)
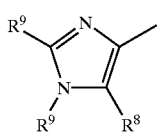
(Z¹³)
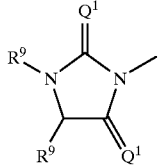
(Z¹⁴)
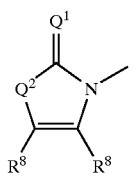
(Z¹⁵)
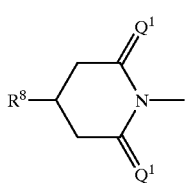
(Z¹⁶)
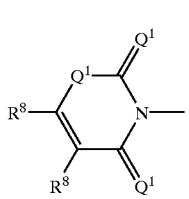
(Z¹⁷)
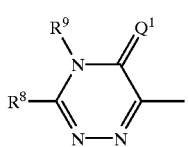
(Z¹⁸)
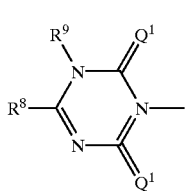
(Z¹⁹)
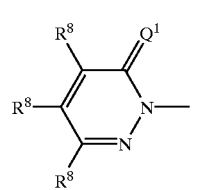
(Z²⁰)
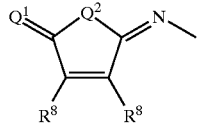
(Z²¹)
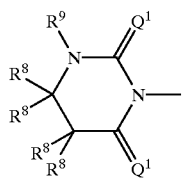
(Z²²)
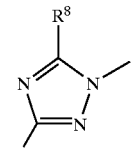
(Z²³)
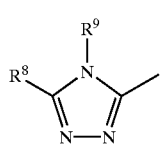
(Z²⁴)
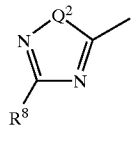
(Z²⁵)
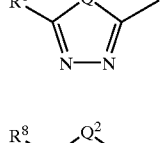
(Z²⁶)
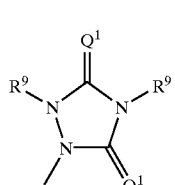
(Z²⁷)
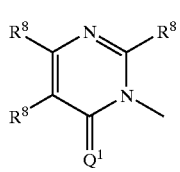
(Z²⁸)

-continued (Z29) 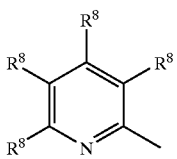

(Z30) 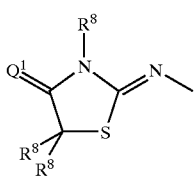

(Z31) 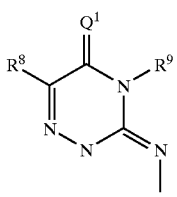

(Z32) 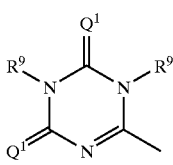

(Z33) 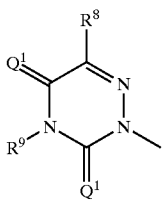

(Z34) 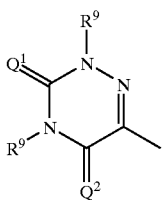

(Z35) 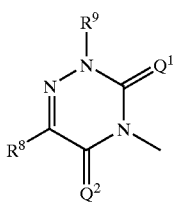

(Z36) 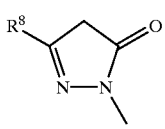

where in each case
$Q^1$ and $Q^2$ have the abovementioned meaning,
$R^8$ represents hydrogen, amino, nitro, cyano, carboxyl, carbamoyl, thiocarbamoyl, fluorine, chlorine, bromine, or represents methyl, ethyl, n- or i-propyl, n-, i-, s- or t-butyl, each of which is optionally substituted by cyano, fluorine, chlorine, methoxy or ethoxy, or represents propenyl, butenyl, propinyl or butinyl, each of which is optionally substituted by fluorine, chlorine or bromine, or represents methoxy, ethoxy, n- or i-propoxy, n-, i-, s- or t-butoxy, methoxycarbonyl or ethoxycarbonyl, each of which is optionally substituted by cyano, fluorine, chlorine, methoxy or ethoxy, or represents propenyloxy, butenyloxy, propinyloxy or butinyloxy, each of which is optionally substituted by fluorine or chlorine, or represents methylthio, ethylthio, n- or i-propylthio, n-, i-, s- or t-butylthio, each of which is optionally substituted by cyano, fluorine, chlorine, methoxy or ethoxy, or represents propenylthio, butenylthio, propinylthio or butinylthio, each of which is optionally substituted by fluorine or chlorine, or represents methylamino, ethylamino, n- or i-propylamino, n-, i-, s- or t-butylamino, dimethylamino or diethylamino, each of which is optionally substituted by cyano, fluorine, chlorine, methoxy or ethoxy, or represents cyclopropyl, cyclobutyl, cyclopentyl, cyclohexyl, cyclopropylmethyl, cyclobutylmethyl, cyclopentylmethyl or cyclohexylmethyl, each of which is optionally substituted by cyano, fluorine, chlorine, bromine, methyl or ethyl, and $R^9$ represents hydrogen, hydroxyl, amino, cyano, or represents methyl, ethyl, n- or i-propyl, n-, i-, s- or t-butyl, each of which is optionally substituted by cyano, fluorine, chlorine, methoxy or ethoxy, or represents propenyl, butenyl, propinyl or butinyl, each of which is optionally substituted by fluorine, chlorine or bromine, or represents methoxycarbonyl or ethoxycarbonyl, each of which is optionally substituted by cyano, fluorine, chlorine, methoxy or ethoxy, or represents cyclopropyl, cyclobutyl, cyclopentyl, cyclohexyl, cyclopropylmethyl, cyclobutylmethyl, cyclopentylmethyl or cyclohexylmethyl, each of which is optionally substituted by cyano, fluorine, chlorine, bromine, methyl or ethyl, or represents phenyl or benzyl, each of which is optionally substituted by cyano, nitro, fluorine, chlorine, bromine, methyl, ethyl, n- or i-propyl, n-, i-, s- or t-butyl, trifluoromethyl, methoxy, ethoxy, n- or i-propoxy, n-, i-, s- or t-butoxy, difluoromethoxy and/or trifluoromethoxy, where, if appropriate, two adjacent radicals—$R^8$ and $R^8$, $R^9$ and $R^9$ or $R^8$ and $R^9$—together represent ethane-1,2-diyl (dimethylene), propane-1,3-diyl (trimethylene), butane-1,4-diyl (tetramethylene) or 1-oxa-butane-1,4-diyl, and where the individual radicals $R^8$ and $R^9$—if they occur more than once in the same heterocyclic group, may have identical or different meanings within the above definition, with the exception of the prior-art compound N-[5-chloro-2-(2,5-dihydro-3,4-dimethyl-2,5-dioxo-1H-pyrrol-1-yl)-phenyl]-acetamide (cf. Indian J. Chem, Sect. B, 29B (1990), 659–660—cited in Chem. Abstracts 113:211906), and of N-[2-(5-diethylamino-3-t-butyl-1H-1,2,4-triazol-1-yl)-5-trifluoromethyl-phenyl]-2,2-dimethyl-propanamide and N-[2-(5-diethylamino-3-t-butyl-1H-1,2,4-triazol-1-yl)-5-trifluoromethyl-phenyl]-acetamide (cf. JP 02091062—cited in Chem. Abstracts 113:97612), which are also prior-art compounds.

Very especially preferred are those compounds of the formula (I)
in which
$R^1$, $R^2$, $R^3$, $R^4$, n, $Q^1$, $Q^2$, $R^5$, $R^6$ and $R^7$ have the meanings given above as being particularly preferred and
Z represents one of the heterocyclic groups which follow.

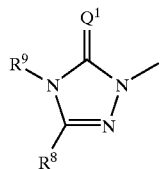

($Z^1$)

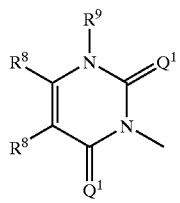

($Z^3$)

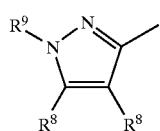

($Z^{11}$)

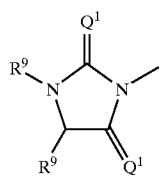

($Z^{13}$)

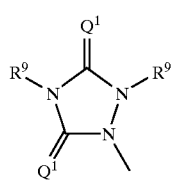

($Z^{27}$)

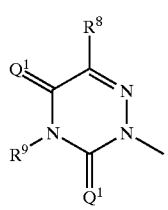

($Z^{33}$)

where in each case
$Q^1$, $Q^2$, $R^8$ and $R^9$ have the meanings given above as being particularly preferred.

The abovementioned general definitions of radicals, or definitions of radicals where preferred ranges have been given, apply to the end products of the formula (I) and, analogously, to the starting materials or intermediates required in each case for the preparation. These definitions of radicals can be combined with each other as desired, that is to say combinations between the preferred ranges given are also possible.

Examples of the compounds of the formula (I) according to the invention are given in the groups which follow.

Group 1

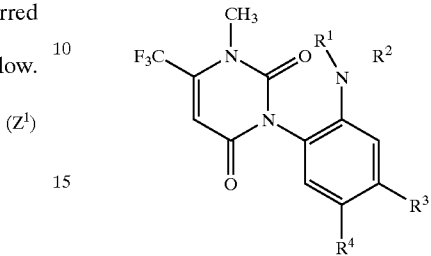

$R^1$, $R^2$, $R^3$ and $R^4$ have the meanings given in the list which follows:

| $R^1$ | $R^2$ | $R^3$ | $R^4$ |
|---|---|---|---|
| H | —CO—CH$_3$ | H | H |
| H | —CO—CH$_3$ | F | H |
| H | —CO—CH$_3$ | Cl | H |
| H | —CO—CH$_3$ | CH$_3$ | H |
| H | —CO—C$_2$H$_5$ | H | H |
| H | —CO—C$_2$H$_5$ | F | H |
| H | —CO—C$_2$H$_5$ | Cl | H |
| H | —CO—C$_2$H$_5$ | CH$_3$ | H |
| H | —CO—C$_3$H$_7$-n | H | H |
| H | —CO—C$_3$H$_7$-n | F | H |
| H | —CO—C$_3$H$_7$-n | Cl | H |
| H | —CO—C$_3$H$_7$-n | CH$_3$ | H |
| H | —CO—C$_3$H$_7$-i | H | H |
| H | —CO—C$_3$H$_7$-i | F | H |
| H | —CO—C$_3$H$_7$-i | Cl | H |
| H | —CO—C$_3$H$_7$-i | CH$_3$ | H |
| H | —CO—C$_3$H$_7$-i | OCH$_3$ | H |
| H | —CO—C$_4$H$_9$-n | H | H |
| H | —CO—C$_4$H$_9$-n | F | H |
| H | —CO—C$_4$H$_9$-n | Cl | H |
| H | —CO—C$_4$H$_9$-n | CH$_3$ | H |
| H | —CO—C$_4$H$_9$-i | H | H |
| H | —CO—C$_4$H$_9$-i | F | H |
| H | —CO—C$_4$H$_9$-i | Cl | H |
| H | —CO—C$_4$H$_9$-i | CH$_3$ | H |
| H | —CO—C$_4$H$_9$-s | H | H |
| H | —CO—C$_4$H$_9$-s | Cl | H |
| H | —CO—C$_4$H$_9$-s | CH$_3$ | H |
| H | —CO—C$_4$H$_9$-s | F | H |
| H | —CO—C$_4$H$_9$-t | H | H |
| H | —CO—C$_4$H$_9$-t | F | H |
| H | —CO—C$_4$H$_9$-t | Cl | H |
| H | —CO—C$_4$H$_9$-t | CH$_3$ | H |
| H | 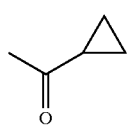 | H | H |
| H | 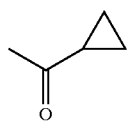 | F | H |

-continued

| R¹ | R² | R³ | R⁴ |
|---|---|---|---|
| H | cyclopropyl-C(=O)- | Cl | H |
| H | cyclopropyl-C(=O)- | CH₃ | H |
| H | phenyl-C(=O)- | H | H |
| H | phenyl-C(=O)- | F | H |
| H | phenyl-C(=O)- | Cl | H |
| H | phenyl-C(=O)- | CH₃ | H |
| H | —CO—CH₃ | H | Cl |
| H | —CO—CH₃ | Br | H |
| H | —CO—CH₃ | CN | H |
| H | —CO—CH₃ | CF₃ | H |
| H | —CO—C₂H₅ | H | Cl |
| H | —CO—C₂H₅ | Br | H |
| H | —CO—C₂H₅ | CN | H |
| H | —CO—C₂H₅ | CF₃ | H |
| H | —CO—C₃H₇-n | H | Cl |
| H | —CO—C₃H₇-n | Br | H |
| H | —CO—C₃H₇-n | CN | H |
| H | —CO—C₃H₇-n | CF₃ | H |
| H | —CO—C₃H₇-i | H | Cl |
| H | —CO—C₃H₇-i | Br | H |
| H | —CO—C₃H₇-i | CN | H |
| H | —CO—C₃H₇-i | CF₃ | H |
| H | —CO—C₃H₇-i | Cl | Cl |
| H | —CO—C₄H₉-n | H | Cl |
| H | —CO—C₄H₉-n | Br | H |
| H | —CO—C₄H₉-n | CN | H |
| H | —CO—C₄H₉-n | CF₃ | H |
| H | —CO—C₄H₉-i | H | Cl |
| H | —CO—C₄H₉-i | Br | H |
| H | —CO—C₄H₉-i | CN | H |
| H | —CO—C₄H₉-i | CF₃ | H |
| H | —CO—C₄H₉-s | H | Cl |
| H | —CO—C₄H₉-s | Br | H |
| H | —CO—C₄H₉-s | CF₃ | H |
| H | —CO—C₄H₉-s | CN | H |
| H | —CO—C₄H₉-t | H | Cl |
| H | —CO—C₄H₉-t | Br | H |
| H | —CO—C₄H₉-t | CN | H |

-continued

| R¹ | R² | R³ | R⁴ |
|---|---|---|---|
| H | —CO—C₄H₉-t | CF₃ | H |
| H | cyclopropyl-C(=O)- | H | Cl |
| H | cyclopropyl-C(=O)- | Br | H |
| H | cyclopropyl-C(=O)- | CN | H |
| H | cyclopropyl-C(=O)- | CF₃ | H |
| H | phenyl-C(=O)- | H | Cl |
| H | phenyl-C(=O)- | Br | H |
| H | phenyl-C(=O)- | CN | H |
| H | phenyl-C(=O)- | CF₃ | H |

Group 2

[Structure: pyrimidine ring with NH₂, CF₃, substituted phenyl bearing N(R¹)(R²), R³, R⁴]

$R^1$, $R^2$ $R^3$ and $R^4$ have, by way of example, the meanings given above in Group 1.

Group 3

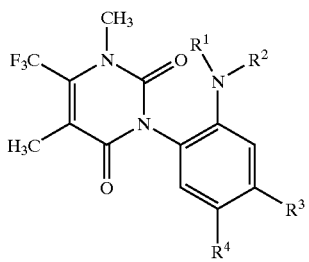

$R^1$, $R^2$ $R^3$ and $R^4$ have, by way of example, the meanings given above in Group 1.

Group 4

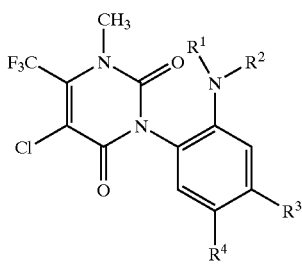

$R^1$, $R^2$ $R^3$ and $R^4$ have, by way of example, the meanings given above in Group 1.

Group 5

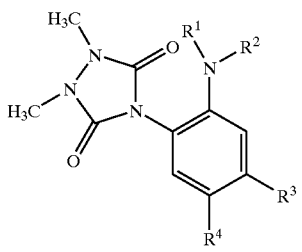

$R^1$, $R^2$ $R^3$ and $R^4$ have, by way of example, the meanings given above in Group 1.

Group 6

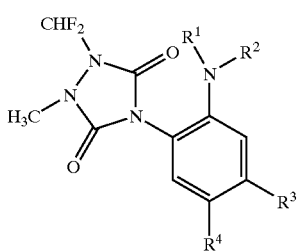

$R^1$, $R^2$ $R^3$ and $R^4$ have, by way of example, the meanings given above in Group 1.

Group 7

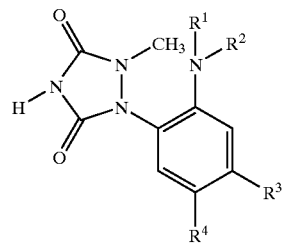

$R^1$, $R^2$ $R^3$ and $R^4$ have, by way of example, the meanings given above in Group 1.

Group 8

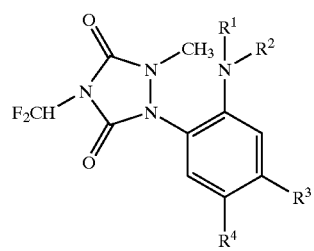

$R^1$, $R^2$ $R^3$ and $R^4$ have, by way of example, the meanings given above in Group 1.

Group 9

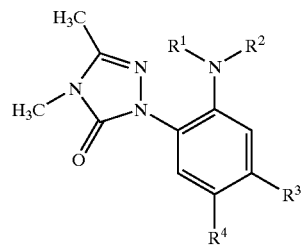

$R^1$, $R^2$ $R^3$ and $R^4$ have, by way of example, the meanings given above in Group 1.

Group 10

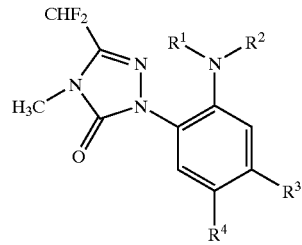

$R^1$, $R^2$ $R^3$ and $R^4$ have, by way of example, the meanings given above in Group 1.

Group 11

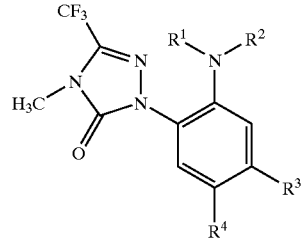

$R^1$, $R^2$ $R^3$ and $R^4$ have, by way of example, the meanings given above in Group 1.

Group 12

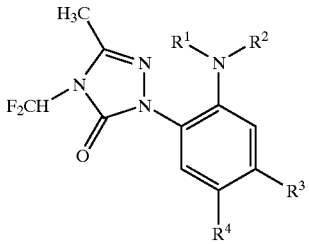

$R^1$, $R^2$ $R^3$ and $R^4$ have, by way of example, the meanings given above in Group 1.

Group 13

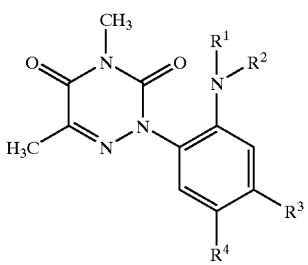

$R^1$, $R^2$ $R^3$ and $R^4$ have, by way of example, the meanings given above in Group 1.

Group 14

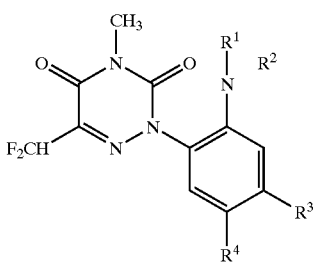

$R^1$, $R^2$ $R^3$ and $R^4$ have, by way of example, the meanings given above in Group 1.

Group 15

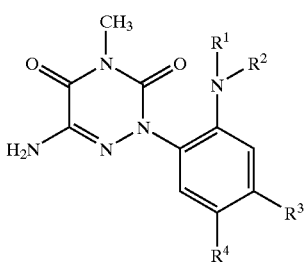

$R^1$, $R^2$ $R^3$ and $R^4$ have, by way of example, the meanings given above in Group 1.

If, for example, 2-(2-amino-4-cyano-phenyl)-4-methyl-5-difluoromethyl-2,4-dihy-dro-3H-1,2,4-triazol-3-one and acetyl chloride are used as starting materials, the course of the reaction in the process according to the invention can be outlined by the following scheme:

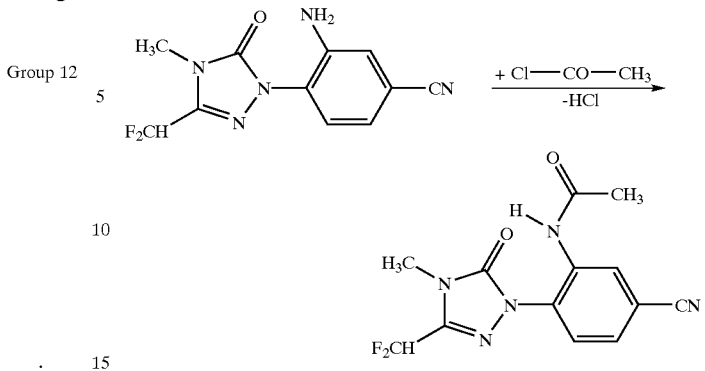

Formula (II) provides the general definition of the aromatic amino compounds to be used as starting materials in the process according to the invention for the preparation of compounds of the formula (I). In formula (II), $R^3$, $R^4$ and Z preferably, or in particular, have those meanings which have already been mentioned above in connection with the description of the compounds of the formula (I) according to the invention as being preferred, or particularly preferred, for $R^3$, $R^4$ and Z; $A^1$ preferably represents hydrogen, hydroxyl, amino, $C_1$–$C_6$-alkyl, $C_1$–$C_6$-alkoxy, $C_1$–$C_6$-alkylamino or di-($C_1$–$C_6$-alkyl)-amino, in particular hydrogen or methyl.

The starting materials of the general formula (II) were hitherto unknown from the literature; being new substances, they are also a subject of the present application.

The new aromatic amino compounds of the general formula (II) are obtained when aromatic nitro compounds of the general formula (IV)

(IV)

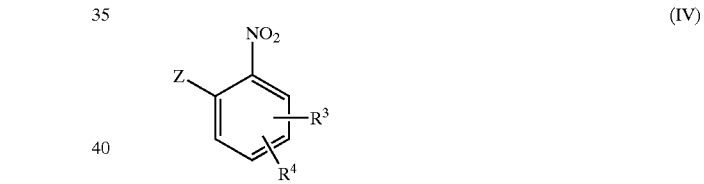

in which $R^3$, $R^4$ and Z have the abovementioned meaning are reacted with reducing agents such as, for example, with hydrogen in the presence of a catalyst, such as, for example, Raney nickel, or with tin(II) chloride dihydrate, or with iron in the presence of an acid such as, for example, hydrochloric acid, in each case in the presence of a diluent such as, for example, water, methanol or ethanol, at temperatures between 0° C. and 120° C. (cf. the preparation examples).

The aromatic nitro compounds of the general formula (IV) which are required as precursors are known and/or can be prepared by known processes (cf. U.S. Pat. No. 3,489,761, DE 2413938, GB 2123420, U.S. Pat. No. 4,496,390, WO 8702357, EP 617026, preparation examples).

Formula (III) provides a general definition of the electrophilic compounds furthermore to be used as starting materials in the process according to the invention for the preparation of compounds of the formula (I). In formula (III), $R^2$ preferably, or in particular, has the meaning which has already been given above in connection with the description of the compounds of the formula (I) according to the invention as preferred, or particularly preferred, for $R^2$; X preferably represents fluorine, chlorine, bromine or iodine, in particular chlorine or bromine.

The starting materials of the general formula (III) are known chemicals for organic synthesis.

The process according to the invention for the preparation of the compounds of the formula (I) is preferably carried out using an acid acceptor. Suitable acid acceptors for the process according to the invention are, generally, the customary inorganic or organic bases or acid binders. These preferably include acetates, amides, carbonates, hydrogen carbonates, hydrides, hydroxides or alkanolates of alkali metals or alkaline earth meals, such as, for example, sodium acetate, potassium acetate, calcium acetate, lithium amide, sodium amide, potassium amide or calcium amide, sodium carbonate, potassium carbonate or calcium carbonate, sodium hydrogen carbonate, potassium hydrogen carbonate, calcium hydrogen carbonate, lithium hydride, sodium hydride, potassium hydride, calcium hydride, lithium hydroxide, sodium hydroxide, potassium hydroxide, calcium hydroxide, sodium methoxide, sodium ethoxide, sodium n- or i-propoxide, sodium n-, i-, s- or t-butoxide, potassium methoxide, potassium ethoxide, potassium n- or i-propoxide or potassium n-, i-, s- or t-butoxide; furthermore also basic organic nitrogen compounds such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2,2,2]-octane (DABCO), 1,5-diazabicyclo[4,3,0]-non-5-ene (DBN), or 1,8-diazabicyclo[5,4,0]-undec-7-ene (DBU).

The process according to the invention for the preparation of the compounds of the formula (I) is preferably carried out using a diluent. Suitable diluents for carrying out the process according to the invention are, especially, inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, carbon tetrachloride; ethers such as diethyl ether, diisopropyl ether, dioxane, tetrahydrofuran, ethylene glycol dimethyl ether or ethylene glycol diethyl ether; ketones, such as acetone, butanone or methyl isobutyl ketone; nitriles such as acetonitrile, propionitrile or butyronitrile; amides such as N,N-dimethylformamide, N,N-dimethylacetamide, N-methyl-formanilide, N-methyl-pyrrolidone or hexamethylphosphoric triamide; esters such as methyl acetate or ethyl acetate, sulphoxides such as dimethyl sulphoxide, alcohols such as methanol, ethanol, n- or i-propanol, ethylene glycol monomethyl ether, ethylene glycol monoethyl ether, diethylene glycol monomethyl ether, diethylene glycol monoethyl ether, their mixtures with water, or pure water.

When carrying out the process according to the invention, the reaction temperatures may be varied within a substantial range. In general, the process is carried out at temperatures between 0° C. and 150° C., preferably between 10° C. and 120° C.

The process according to the invention is generally carried out under atmospheric pressure. However, it is also possible to carry out the process according to the invention under elevated or reduced pressure, in general between 0.1 bar and 10 bar.

To carry out the process according to the invention, the starting materials are generally employed in approximately equimolar amounts. However, it is also possible to use one of the components in a larger excess. In general, the reaction is carried out in a suitable diluent in the presence of a reaction auxiliary, and the reaction mixture is generally stirred for several hours at the temperature required. Working-up is carried out by customary methods (cf. the preparation examples).

The active compounds according to the invention can be used as defoliants, desiccants, haulm killers and, in particular, as herbicides. Weeds in the broadest sense are to be understood as meaning all plants which are grown in locations where they are undesired. Whether the substances according to the invention act as total or selective herbicides depends essentially on the quantity applied.

The active compounds according to the invention can be used, for example, on the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindemia, ILamium, Veronica, Abutilon, Emex, Datura, Viola, Galeopsis, Papaver, Centaurea, Trifolium, Ranunculus, Taraxacum.

Dicotyledonous crops of the genera: Gossypium, Glycine, Beta, Daucus, Phaseoltis, Pisum, Solanum, Linum, lpomoea, Vicia, Nicotiana, Lycopersicon, Arachis, Brassica, Lactuca, Cucumis, Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera.

Monocotyledonous crops of the genera: Oryza, Zea, Triticum, Hordeum, Avena, Secale, Sorghum, Panicum, Saccharum, Ananas, Asparagus, Allium.

However, the use of the active compounds according to the invention is in no way restricted to these genera, but equally extends to other plants.

Depending on the concentration, the compounds are suitable for the total control of weeds on, for example, industrial terrain and rail tracks and on paths and squares with or without tree plantings. Equally, the compounds may be employed for controlling weeds in perennial crops, for example afforestations, plantings of woody ornamentals, orchards, vineyards, citrus orchards, nut orchards, banana plantations, coffee plantations, tea plantations, rubber plantations, oil palm plantations, cocoa plantations, soft fruit plantings, hop plantings, on ornamental lawns, turf and pastures, and for the selective control of weeds in annual crops.

The compounds of the formula (I) according to the invention are particularly suitable for the selective control of monocotyledonous and dicotyledonous weeds in monocotyledonous crops such as, for example, in wheat, both pre- and post-emergence.

The active compounds can be converted into the customary formulations such as solutions, emulsions, wettable powders, suspensions, powders, dusts, pastes, soluble powders, granules, suspoemulsion concentrates, natural and synthetic products impregnated with active compound, and microencapsulations in polymeric substances.

These formulations are prepared in the known manner, for example by mixing the active compounds with extenders, that is to say liquid solvents and/or solid carriers, if appropriate using surfactants, that is to say emulsifiers and/or dispersants and/or foam formers.

If water is used as extender, it is also possible, for example, to use organic solvents as auxiliary solvents. Suitable liquid solvents are essentially: aromatics such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane, or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and water.

Examples of suitable solid carriers are: ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite, dolomite, and synthetic granules of inorganic or organic meals and granules of organic material such as sawdust, coconut shells, maize cobs and tobacco stalks; suitable emulsifiers and/or foam formers are: for example non-ionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin-sulphite waste liquors and methylcellulose.

Adhesives such as carboxymethylcellulose, natural and synthetic polymers in the form of powders, granules or latices such as gum arabic, polyvinyl alcohol, polyvinyl acetate, and natural phospholipids such as cephalins and lecithins and synthetic phospholipids may be used in the formulations. Other additives may be mineral and vegetable oils.

Colorants such as inorganic pigments, for example iron oxide, titanium oxide, Prussian Blue, and organic dyestuffs such as alizarin, azo and metal phthalocyanin dyes and micronutrients such as salts of iron, manganese, boron, copper, cobalt, molybdenum and zinc may be used.

The formulations generally comprise between 0.1 and 95% by weight of active compound, preferably between 0.5 and 90%.

The active compounds according to the invention, as such, or in their formulations, may also be used for controlling weeds as a mixture with known herbicides, readymixes or tank mixes being possible.

Suitable known herbicides for the mixtures are, for example acetochlor, acifluorfen(-sodium), aclonifen, alachlor, alloxydim(-sodium), ametryne, amidochlor, amidosulphuron, asulam, atrazine, azimsulphuron, benazolin, benfuresate, bensulphuron(-methyl), bentazone, benzofenap, benzoylprop(-ethyl), bialaphos, bifenox, bromobutide, bromofenoxim, bromoxynil, butachlor, butylate, cafenstrole, carbetamide, chlomethoxyfen, chloramben, chloridazon, chlorimuron(-ethyl), chlornitrofen, chlorsulphuron, chlortoluron, cinmethylin, cinosulphuron, clethodim, clodinafop(-propargyl), clomazone, clopyralid, clopyrasulphuron, cloransulam (-methyl), cumyluron, cyanazine, cycloate, cyclosulphamuron, cycloxydim, cyhalofop(-butyl), 2,4-D, 2,4-DB, 2,4-DP, desmedipham, di-allate, dicamba, diclofop(-methyl), difenzoquat, diflufenican, dimefuron, dimepiperate, dimethachlor, dimethametryn, dimethenamid, dinitramine, diphenamid, diquat, dithiopyr, diuron, dymron, EPTC, esprocarb, ethalfluralin, ethametsulphuron(-methyl), ethofumesate, ethoxyfen, etobenzanid, fenoxaprop(-ethyl), flamprop(-isopropyl), flamprop(-isopropyl-L), flamprop(-methyl), flazasulphuron, fluazifop(-butyl), flumetsulam, flumiclorac(-pentyl), flumioxazin, flumipropyn, fluometuron, fluorochloridone, fluoroglycofen(-ethyl), flupoxam, flupropacil, flurenol, fluridone, fluroxypyr, flurprimidol, flurtamone, fomesafen, glufosinate(-ammonium), glyphosate(-isopropylammonium), halosafen, haloxyfop(-ethoxyethyl), hexazinone, imazamethabenz(-methyl), imazamethapyr, imazamox, imazapyr, imazaquin, imazethapyr, imazosulphuron, ioxynil, isopropalin, isoproturon, isoxaben, isoxaflutole, isoxapyrifop, lactofen, lenacil, linuron, MCPA, MCPP, mefenacet, metamitron, metazachlor, methabenzthiazuron, metobenzuron, metobromuron, metolachlor, metosulam, metoxuron, metribuzin, metsulphuron(-methyl), molinate, monolinuron, naproanilide, napropamide, neburon, nicosulphuron, norflurazon orbencarb, oryzalin, oxadiazon, oxyfluorfen, paraquat, pendimethalin, phenmedipham, piperophos, pretilachlor, primisulphuron(-methyl), prometryn, propachlor, propanil, propaquizafop, propyzamide, prosulphocarb, prosulphuron, pyrazolate, pyrazosulphuron(-ethyl), pyrazoxyfen, pyributicarb, pyridate, pyrithiobac(-sodium), quinchlorac, quinmerac, quizalofop(-ethyl), quizalofop(-p-tefuryl), rimsulphuron, sethoxydim, simazine, simetryn, sulcotrione, sulphentrazone, sulphometuron(-methyl), sulphosate, tebutam, tebuthiuron, terbuthylazine, terbutryn, thenylchlor, thiafluamide, thiazopyr, thidiazimin, thifensulphuron(-methyl), thiobencarb, thiocarbazil, tralkoxydim, tri-allate, triasulphuron, tribenuron(-methyl), triclopyr, tridiphane, trifluralin and triflusulphuron.

A mixture with other known active compounds such as fungicides, insecticides, akaricides, nematicides, bird repellants, plant nutrients and soil conditioners is also possible.

The active compounds can be applied as such, in the form of their formulations or the use forms prepared therefrom by further dilution, such as ready-to-use solutions, suspensions, emulsions, powders, pastes and granules. The application is effected in the customary manner, for example by pouring, spraying, atomizing or broadcasting.

The active compounds according to the invention can be applied before or after plant emergence. They may also be incorporated into the soil prior to planting.

The application rate of active compound may vary within a substantial range. It depends essentially on the nature of the desired effect. In general, the application rates are between 1 g and 10 kg of active compound per hectare of ground surface, preferably between 5 g and 5 kg per ha.

The preparation and the use of the active compounds according to the invention can be seen from the examples which follow.

PREPARATION EXAMPLES

Example 1

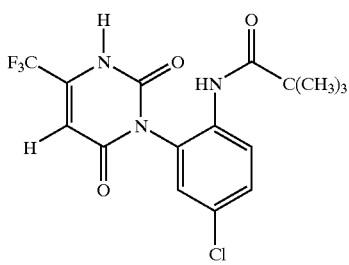

A mixture of 1.6 g (5.23 mmol) of 1-(2-amino-5-chloro-phenyl)-3,6-dihydro-2,6-dioxo-4-trifluoromethyl-1(2H)-pyrimidine, 0.72 g (5.23 mmol) of pivaloyl chloride, 1.21 g (12 mmol) of triethylamine and 30 ml of acetonitrile is stirred for 45 minutes at room temperature (approx. 20° C.) and subsequently concentrated under a water pump vacuum. The residue is then stirred with IN hydrochloric acid, diethyl ether and petroleum ether, and the product obtained as crystals is isolated by filtration with suction.

This gives 1.65 g (81% of theory) of 1-(5-chloro-2-pivaloylamino-phenyl)-3,6-dihydro-2,6-dioxo-4-trifluoromethyl-1(2H)-pyrimidine of melting point 276° C.

Example 2

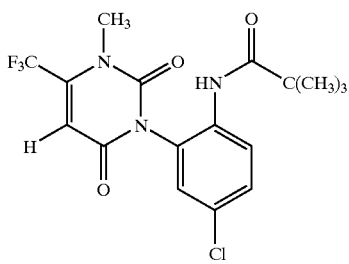

A mixture of 1.17 g (3 mmol) of 1-(5-chloro-2-pivaloylamino-phenyl)-3,6-dihydro-2,6-dioxo-4-trifluoromethyl-1(2H)-pyrimidine, 0.42 g (3 mmol) of dimethylsulphate, 0.46 g (3 mmol) of potassium carbonate and 20 ml of acetone is refluxed for 45 minutes and subsequently concentrated under a water pump vacuum. The residue is then stirred with IN hydrochloric acid, ethyl acetate and diethyl ether. The product, which is obtained as crystals, is isolated by filtration with suction.

This gives 1.05 g (88% of theory) of 1-(5-chloro-2-pivaloylamino-phenyl)-3,6-dihydro-2,6-dioxo-3-methyl-4-trifluoromethyl-1(2H)-pyrimidine of melting point 267° C.

Other examples of the compounds of the formula (I) which can be prepared analogously to preparation examples 1 and 2 and following the general description of the preparation process according to the invention are those given in the tables below.

$$\text{(I)}$$

Many of the active compounds according to the invention may be represented by the general formula (Ia) below:

$$\text{(Ia)}$$

TABLE 1a

Examples of the compounds of the formula (Ia)

| Ex No. | $R^1$ | $R^2$ | $R^3$ | $R^4$ | Z | Melting point (° C.) |
|---|---|---|---|---|---|---|
| 3 | H | —CO—$C_3H_7$-i | H | H | 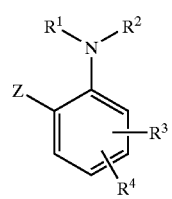 | (amorphous) |
| 4 | H | —CO—$C_3H_7$-i | Cl | H | 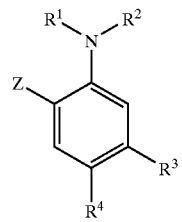 | 149 |

TABLE 1a-continued

Examples of the compounds of the formula (Ia)

| Ex No. | R¹ | R² | R³ | R⁴ | Z | Melting point (° C.) |
|---|---|---|---|---|---|---|
| 5 | H | —CO—cyclopropyl | Cl | H | 6-(CF₃)-3-methyl-4-oxo-3,4-dihydropyrimidin-1-yl | (amorphous) |
| 6 | H | —CO—(2-F-C₆H₄) | Cl | H | 6-(CF₃)-3-methyl-4-oxo-3,4-dihydropyrimidin-1-yl | (amorphous) |
| 7 | H | —CO—C₄H₉-t | Cl | H | 6-(CF₃)-3-methyl-4-oxo-3,4-dihydropyrimidin-1-yl | 184 |
| 8 | H | —CO—CH₃ | Cl | H | 6-(CF₃)-3-methyl-4-oxo-3,4-dihydropyrimidin-1-yl | (amorphous) |
| 9 | H | —CO—CF₃ | Cl | H | 6-(CF₃)-3-methyl-4-oxo-3,4-dihydropyrimidin-1-yl | (amorphous) |
| 10 | H | —CO—(4-Cl-C₆H₄) | Cl | H | 6-(CF₃)-3-methyl-4-oxo-3,4-dihydropyrimidin-1-yl | (amorphous) |
| 11 | H | —CO—cyclopropyl | H | Cl | 6-(CF₃)-3-methyl-2,4-dioxo-1,2,3,4-tetrahydropyrimidin-1-yl | 260 |
| 12 | H | —CO—CH₃ | H | Cl | 6-(CF₃)-3-methyl-2,4-dioxo-1,2,3,4-tetrahydropyrimidin-1-yl | 260 |

TABLE 1a-continued

Examples of the compounds of the formula (Ia)

| Ex No. | R¹ | R² | R³ | R⁴ | Z | Melting point (° C.) |
|---|---|---|---|---|---|---|
| 13 | H | -CO-cyclopropyl | H | Cl | 1,3-dimethyl-6-(trifluoromethyl)uracil | 208 |
| 14 | H | —CO—CH$_3$ | H | Cl | 1,3-dimethyl-6-(trifluoromethyl)uracil | 218 |
| 15 | H | —CO—C$_4$H$_9$-t | Cl | H | 3-methyl-6-(trifluoromethyl)uracil (NH) | 267 |
| 16 | H | -CO-cyclopropyl | Cl | H | 3-methyl-6-(trifluoromethyl)uracil (NH) | 227 |
| 17 | H | —CO—CH$_3$ | Cl | H | 3-methyl-6-(trifluoromethyl)uracil (NH) | 294 |
| 18 | H | —CO—C$_4$H$_9$-t | Cl | H | 1,3-dimethyl-6-(trifluoromethyl)uracil | 209 |
| 19 | H | -CO-cyclopropyl | Cl | H | 1,3-dimethyl-6-(trifluoromethyl)uracil | 205 |

TABLE 1a-continued

Examples of the compounds of the formula (Ia)

| Ex No. | R¹ | R² | R³ | R⁴ | Z | Melting point (° C.) |
|---|---|---|---|---|---|---|
| 20 | H | —CO—CH₃ | Cl | H | 1,3-dimethyl-6-(trifluoromethyl)uracil | 223 |
| 21 | H | 4-chlorophenacyl | Cl | H | 3-methyl-6-(trifluoromethyl)uracil (NH) | 251 |
| 22 | H | —CO—C₃H₇-i | Cl | H | 3-methyl-6-(trifluoromethyl)uracil (NH) | 221 |
| 23 | H | 4-chlorophenacyl | Cl | H | 1,3-dimethyl-6-(trifluoromethyl)uracil | 225 |
| 24 | H | —CO—C₃H₇-i | Cl | H | 1,3-dimethyl-6-(trifluoromethyl)uracil | 205 |
| 25 | H | —CO—C₄H₉-t | CH₃ | H | 3-methyl-6-(trifluoromethyl)uracil (NH) | 265 |
| 26 | H | —CO—C₄H₉-t | CH₃ | H | 1,3-dimethyl-6-(trifluoromethyl)uracil | 185 |

TABLE 1a-continued

Examples of the compounds of the formula (Ia)

| Ex No. | $R^1$ | $R^2$ | $R^3$ | $R^4$ | Z | Melting point (°C.) |
|---|---|---|---|---|---|---|
| 27 | H | -CO-cyclopropyl | $CH_3$ | H | 6-$CF_3$, 3-$CH_3$ uracil (NH) | 253 |
| 28 | H | -CO-$C_3H_7$-i | $CH_3$ | H | 6-$CF_3$, 3-$CH_3$ uracil (NH) | 227 |
| 29 | H | -CO-cyclopropyl | $CH_3$ | H | 6-$CF_3$, 1,3-di$CH_3$ uracil | 224 |
| 30 | H | -CO-$C_3H_7$-i | $CH_3$ | H | 6-$CF_3$, 1,3-di$CH_3$ uracil | 174 |
| 31 | H | -CO-$C_4H_9$-t | H | H | 6-$CF_3$, 3-$CH_3$ uracil (NH) | 252 |
| 32 | H | -CO-$C_3H_7$-i | H | H | 6-$CF_3$, 3-$CH_3$ uracil (NH) | 252 |
| 33 | H | -CO-$C_4H_9$-t | H | H | 6-$CF_3$, 1,3-di$CH_3$ uracil | 209 |

TABLE 1a-continued
Examples of the compounds of the formula (Ia)
| Ex No. | R¹ | R² | R³ | R⁴ | Z | Melting point (° C.) |
|---|---|---|---|---|---|---|
| 34 | H | 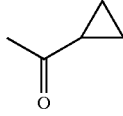 | H | H | 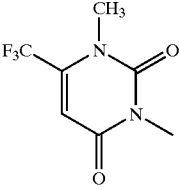 | 187 |
| 35 | H | —CO—C₃H₇-i | H | H | 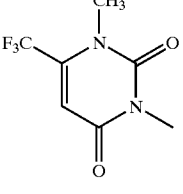 | 171 |
| 36 | H | —CO—CF₃ | Cl | H | 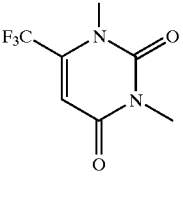 | 245 |
| 37 | H | —CO—CF₃ | Cl | H | 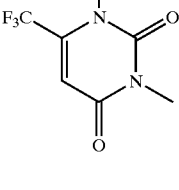 | 175 |
| 38 | H | —SO₂—CH₃ | Cl | H | 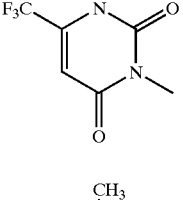 | 212 |
| 39 | CH₃ | —CO—CF₃ | Cl | H | 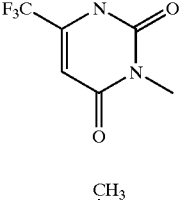 | 196 |
| 40 | H | 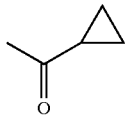 | CF₃ | H | 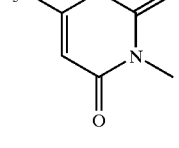 | 229 |

TABLE 1a-continued

Examples of the compounds of the formula (Ia)

| Ex No. | R¹ | R² | R³ | R⁴ | Z | Melting point (° C.) |
|---|---|---|---|---|---|---|
| 41 | H | —CO—C₃H₇-i | CF₃ | H | 1,3-dimethyl-6-(trifluoromethyl)uracil-N | 215 |
| 42 | H | —CO-cyclopropyl | F | H | 6-(trifluoromethyl)-3-methyluracil-N (NH) | 253 |
| 43 | H | —CO—C₃H₇-i | F | H | 6-(trifluoromethyl)-3-methyluracil-N (NH) | 236 |
| 44 | H | —CO-cyclopropyl | F | H | 1,3-dimethyl-6-(trifluoromethyl)uracil-N | 125 |
| 45 | H | —CO—C₃H₇-i | F | H | 1,3-dimethyl-6-(trifluoromethyl)uracil-N | 144 |
| 46 | H | —CO-cyclopropyl | Cl | Cl | 1,3-dimethyl-6-(trifluoromethyl)uracil-N | 225 |
| 47 | H | —CO—C₃H₇-i | Cl | Cl | 1,3-dimethyl-6-(trifluoromethyl)uracil-N | 242 |

TABLE 1a-continued
Examples of the compounds of the formula (Ia)
| Ex No. | R¹ | R² | R³ | R⁴ | Z | Melting point (° C.) |
|---|---|---|---|---|---|---|
| 48 | H | 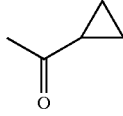 | Br | H | 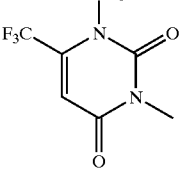 | 211 |
| 49 | H | 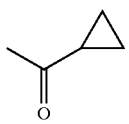 | CN | H | 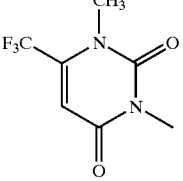 | 217 |
| 50 | H | 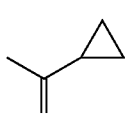 | OCH₃ | H | 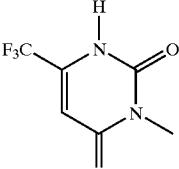 | 230 |
| 51 | H | —CO—C₃H₇-i | OCH₃ | H | 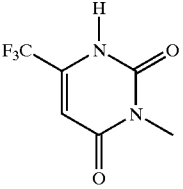 | 177 |
| 52 | H | 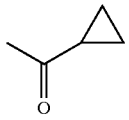 | OCH₃ | H | 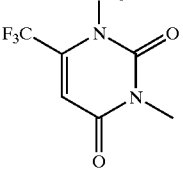 | 159 |
| 53 | H | —CO—C₃H₇-i | OCH₃ | H | 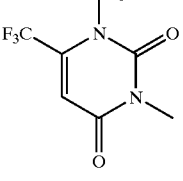 | 114 |
| 54 | H | 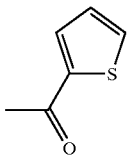 | Cl | H | 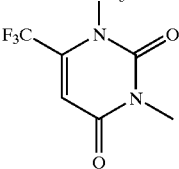 | 181 |

TABLE 1a-continued
Examples of the compounds of the formula (Ia)
| Ex No. | R¹ | R² | R³ | R⁴ | Z | Melting point (° C.) |
|---|---|---|---|---|---|---|
| 55 | H | 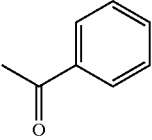 | F | H | 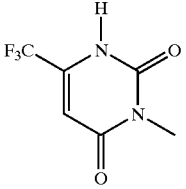 | 240 |
| 56 | H | 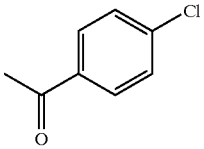 | F | H | 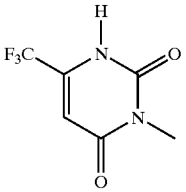 | 220 |
| 57 | H | 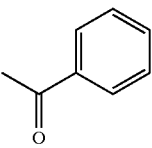 | F | H | 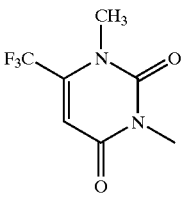 | (amorphous) |
| 58 | H | 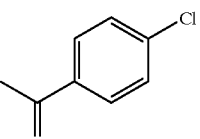 | F | H | 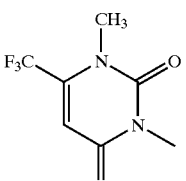 | 202 |
| 59 | H | 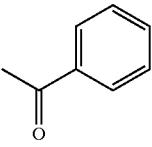 | Cl | H | 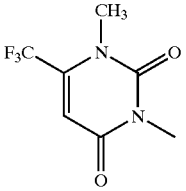 | 175 |
| 60 | H | 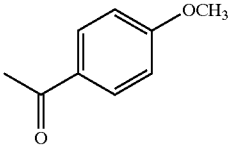 | Cl | H | 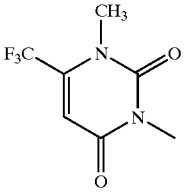 | 105 |
| 61 | 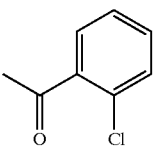 | 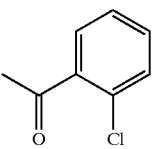 | Cl | H | 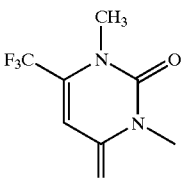 | 134 |

TABLE 1a-continued
Examples of the compounds of the formula (Ia)
| Ex No. | R¹ | R² | R³ | R⁴ | Z | Melting point (° C.) |
|---|---|---|---|---|---|---|
| 62 | 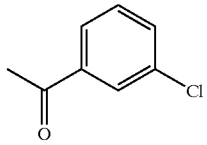 | 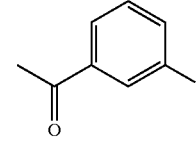 | Cl | H | 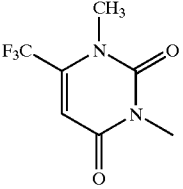 | 193 |
| 63 | H | 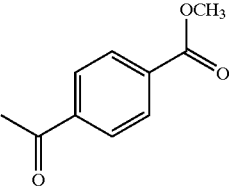 | Cl | H | 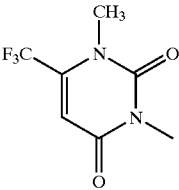 | 205 |
| 64 | H | 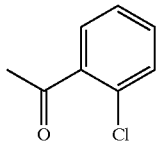 | Cl | H | 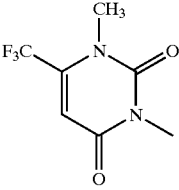 | 225 |
| 65 | H | 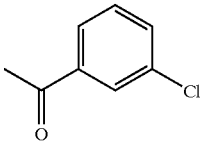 | Cl | H | 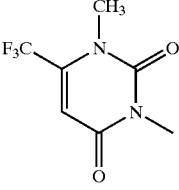 | 156 |
| 66 | H | —CO—CH₃ | H | H | 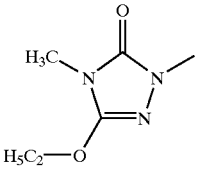 | 120 |
| 67 | H | 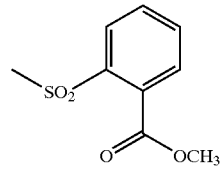 | H | H | 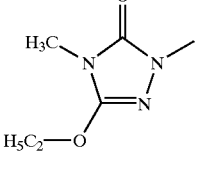 | 153 |
| 68 | H | 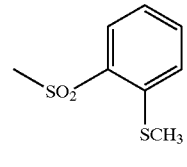 | H | H | 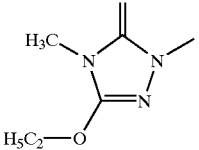 | 120 |

TABLE 1a-continued

Examples of the compounds of the formula (Ia)

| Ex No. | R¹ | R² | R³ | R⁴ | Z | Melting point (° C.) |
|---|---|---|---|---|---|---|
| 69 | H | 2-chloro-benzoyl (acetyl-2-Cl-phenyl) | H | H | 4-methyl-2-methyl-5-ethoxy-1,2,4-triazol-3(4H)-one | 128 |
| 70 | H | 4-chloro-acetylphenyl | H | H | 4-methyl-2-methyl-5-ethoxy-1,2,4-triazol-3(4H)-one | 96 |
| 71 | H | 4-methoxy-acetylphenyl | H | H | 4-methyl-2-methyl-5-ethoxy-1,2,4-triazol-3(4H)-one | 73 |
| 72 | H | 4-methyl-2-methylsulfonyl-fluorophenyl | H | H | 4-methyl-2-methyl-5-ethoxy-1,2,4-triazol-3(4H)-one | 129 |
| 73 | H | 2-methylsulfonyl-benzoic acid ethyl ester | H | H | 4-methyl-2-methyl-5-ethoxy-1,2,4-triazol-3(4H)-one | 108 |
| 74 | H | 2-methylsulfonyl-chloromethyl-phenyl | H | H | 4-methyl-2-methyl-5-ethoxy-1,2,4-triazol-3(4H)-one | 180 |
| 75 | H | 2-methylsulfonyl-chlorophenyl | H | H | 4-methyl-2-methyl-5-ethoxy-1,2,4-triazol-3(4H)-one | 156 |
| 76 | H | 2-methylsulfonyl-2,4-dichlorophenyl | H | H | 4-methyl-2-methyl-5-ethoxy-1,2,4-triazol-3(4H)-one | 132 |

TABLE 1a-continued

Examples of the compounds of the formula (Ia)

| Ex No. | R¹ | R² | R³ | R⁴ | Z | Melting point (° C.) |
|---|---|---|---|---|---|---|
| 77 | H | 2-(OCF₃)-6-(SO₂CH₃)-phenyl (SO₂CH₃, OCF₃ on benzene) | H | H | 4-methyl-2-methyl-5-ethoxy-2,4-dihydro-3H-1,2,4-triazol-3-one | 130 |
| 78 | H | 2-(CF₃)-phenyl-SO₂CH₃ | H | H | 4-methyl-2-methyl-5-ethoxy-2,4-dihydro-3H-1,2,4-triazol-3-one | 187 |
| 79 | H | 4-CF₃-2-Cl-phenyl-SO₂CH₃ | H | H | 4-methyl-2-methyl-5-ethoxy-2,4-dihydro-3H-1,2,4-triazol-3-one | 88 |
| 80 | H | 2-(SCH₃)-phenyl-SO₂CH₃ | H | H | 4-methyl-2-methyl-2,4-dihydro-3H-1,2,4-triazol-3-one | 167 |
| 81 | H | 2-(SC₂H₅)-phenyl-SO₂CH₃ | H | H | 4-methyl-2-methyl-2,4-dihydro-3H-1,2,4-triazol-3-one | 130 |
| 82 | H | 5-CH₃-2-F-phenyl-SO₂CH₃ | H | H | 4-methyl-2-methyl-2,4-dihydro-3H-1,2,4-triazol-3-one | 177 |
| 83 | H | 2-(CO₂CH₃)-phenyl-SO₂CH₃ | H | H | 4-methyl-2-methyl-2,4-dihydro-3H-1,2,4-triazol-3-one | 193 |
| 84 | H | 2-(CO₂C₂H₅)-phenyl-SO₂CH₃ | H | H | 4-methyl-2-methyl-2,4-dihydro-3H-1,2,4-triazol-3-one | 126 |

TABLE 1a-continued

Examples of the compounds of the formula (Ia)

| Ex No. | R¹ | R² | R³ | R⁴ | Z | Melting point (° C.) |
|---|---|---|---|---|---|---|
| 85 | H | 2-(chloromethyl)phenyl-SO₂- (with CH₂Cl ortho) | H | H | 4-methyl-1-methyl-1,2,4-triazol-5(4H)-one | 143 |
| 86 | H | 2-chlorophenyl-SO₂- | H | H | 4-methyl-1-methyl-1,2,4-triazol-5(4H)-one | 150 |
| 87 | H | 2,4-dichlorophenyl-SO₂- | H | H | 4-methyl-1-methyl-1,2,4-triazol-5(4H)-one | 189 |
| 88 | H | 2-(trifluoromethyl)phenyl-SO₂- | H | H | 4-methyl-1-methyl-1,2,4-triazol-5(4H)-one | 154 |
| 89 | H | 2-chloro-6-(trifluoromethyl)phenyl-SO₂- | H | H | 4-methyl-1-methyl-1,2,4-triazol-5(4H)-one | 147 |
| 90 | H | 2-chloro-6-methylphenyl-SO₂- | H | H | 4-methyl-1-methyl-1,2,4-triazol-5(4H)-one | 147 |
| 91 | H | 2-chlorophenyl-C(O)- | H | H | 4-methyl-1-methyl-1,2,4-triazol-5(4H)-one | 128 |
| 92 | H | —CO—CH₂Cl | H | H | 1-methyl-4-isopropyl-2-methyl-1,2,4-triazolidine-3,5-dione | 81 |

TABLE 1a-continued

Examples of the compounds of the formula (Ia)

| Ex No. | R¹ | R² | R³ | R⁴ | Z | Melting point (° C.) |
|---|---|---|---|---|---|---|
| 93 | H | —CO—CH₃ | H | H | 1,2-dimethyl-4-cyclopropyl-1,2,4-triazolidine-3,5-dione | 154 |
| 94 | H | CH₃—CH(Cl)—CO—CH₃ (3-chlorobutan-2-one) | H | H | 1,2-dimethyl-4-cyclopropyl-1,2,4-triazolidine-3,5-dione | 74 |
| 95 | H | —CO—C₂H₅ | H | H | 1,2-dimethyl-4-isopropyl-1,2,4-triazolidine-3,5-dione | 77 |
| 96 | H | —CO—C₂H₅ | H | H | 1,2-dimethyl-4-cyclopropyl-1,2,4-triazolidine-3,5-dione | 89 |
| 97 | H | CH₃—CH(Cl)—CO—CH₃ | H | H | 1,2-dimethyl-4-isopropyl-1,2,4-triazolidine-3,5-dione | 87 |
| 98 | H | —CO—CH₃ | H | H | 1,2-dimethyl-4-isopropyl-1,2,4-triazolidine-3,5-dione | 81 |
| 99 | H | —CO—CH₂Cl | H | H | 1,2-dimethyl-4-cyclopropyl-1,2,4-triazolidine-3,5-dione | 93 |
| 100 | H | —CO—C₂H₅ | H | H | 1,2-dimethyl-4-isopropyl-1,2,4-triazolidine-3,5-dione | 139 |

TABLE 1a-continued

Examples of the compounds of the formula (Ia)

| Ex No. | R¹ | R² | R³ | R⁴ | Z | Melting point (° C.) |
|---|---|---|---|---|---|---|
| 101 | H | —CO—C$_2$H$_5$ | H | H | 4-cyclopropyl-1,2-dimethyl-1,2,4-triazolidine-3,5-dione | 165 |
| 102 | H | —C(=S)—NH—C$_2$H$_5$ | H | H | 4-cyclopropyl-1,2-dimethyl-1,2,4-triazolidine-3,5-dione | 90 |
| 103 | H | —CO-cyclopropyl | H | H | 4-cyclopropyl-1-ethyl-2-methyl-1,2,4-triazolidine-3,5-dione | 138 |
| 104 | H | —CO—CH$_3$ | H | H | 4-cyclopropyl-1-ethyl-2-methyl-1,2,4-triazolidine-3,5-dione | 94 |
| 105 | H | —CO—C$_3$H$_7$-i | H | H | 4-cyclopropyl-1-ethyl-2-methyl-1,2,4-triazolidine-3,5-dione | 116 |
| 106 | H | —CO—C$_2$H$_5$ | H | H | 4-cyclopropyl-1-ethyl-2-methyl-1,2,4-triazolidine-3,5-dione | 70 |
| 107 | H | —C(=O)—NH—C$_3$H$_7$-i | H | H | 4-cyclopropyl-1-ethyl-2-methyl-1,2,4-triazolidine-3,5-dione | 119 |
| 108 | H | —CO—CH$_3$ | H | H | 1-methyl-3-trifluoromethyl-5-oxo-4,5-dihydro-1H-pyrazole | 47 |
| 109 | H | —CO—C$_3$H$_7$-i | H | H | 1-methyl-3-trifluoromethyl-5-oxo-4,5-dihydro-1H-pyrazole | 148 |

TABLE 1a-continued

Examples of the compounds of the formula (Ia)

| Ex No. | R$^1$ | R$^2$ | R$^3$ | R$^4$ | Z | Melting point (° C.) |
|---|---|---|---|---|---|---|
| 110 | H | —CO—C$_2$H$_5$ | H | H | 3-CF$_3$, 1-methyl-pyrazol-5(4H)-one | 165 |
| 111 | H | —CO-cyclopropyl | H | H | 3-CF$_3$, 1-methyl-pyrazol-5(4H)-one | 178 |
| 112 | H | —CO—CH$_3$ | Cl | H | 1,2-dimethyl-4-cyclopropyl-1,2,4-triazolidine-3,5-dione | 67 |
| 113 | H | —CO—C$_3$H$_7$-i | Cl | H | 1,2-dimethyl-4-cyclopropyl-1,2,4-triazolidine-3,5-dione | 147 |
| 114 | H | —CO—C$_2$H$_5$ | Cl | H | 1,2-dimethyl-4-cyclopropyl-1,2,4-triazolidine-3,5-dione | 85 |
| 115 | H | —CO-cyclopropyl | Cl | H | 1,2-dimethyl-4-cyclopropyl-1,2,4-triazolidine-3,5-dione | 155 |
| 116 | H | —CO—CH$_3$ | H | CH$_3$ | 1,2-dimethyl-4-cyclopropyl-1,2,4-triazolidine-3,5-dione | 124 |
| 117 | H | —CO—CH$_2$Cl | H | CH$_3$ | 1,2-dimethyl-4-cyclopropyl-1,2,4-triazolidine-3,5-dione | 136 |

TABLE 1a-continued

Examples of the compounds of the formula (Ia)

| Ex No. | R¹ | R² | R³ | R⁴ | Z | Melting point (° C.) |
|---|---|---|---|---|---|---|
| 118 | H | -CH₂-CO-C(CH₃)₃ | H | CH₃ | 1,2-dimethyl-4-cyclopropyl-1,2,4-triazolidine-3,5-dione | (amorphous) |
| 119 | H | -CO-cyclopropyl | H | CH₃ | 1,2-dimethyl-4-cyclopropyl-1,2,4-triazolidine-3,5-dione | (amorphous) |
| 120 | H | -CO-cyclopropyl | CF₃ | H | 1,2-dimethyl-4-cyclopropyl-1,2,4-triazolidine-3,5-dione | 172 |
| 121 | H | -CO-cyclopropyl | F | H | 2,4-dimethyl-1,2,4-triazine-3,5-dione | ¹H NMR (DMSO-D₆, δ): 0.80–0.81; 3.25; 7.40–7.48; 9.63 ppm |
| 122 | H | -CO-cyclopropyl | H | H | 2,4-dimethyl-5-trifluoromethyl-2,4-dihydro-3H-1,2,4-triazol-3-one | (amorphous) |
| 124 | H | -CO-cyclopropyl | H | CH₃ | 2,4-dimethyl-5-trifluoromethyl-2,4-dihydro-3H-1,2,4-triazol-3-one | (amorphous) |
| 125 | H | —CO—C₃H₇-i | H | CH₃ | 2,4-dimethyl-5-trifluoromethyl-2,4-dihydro-3H-1,2,4-triazol-3-one | 117 |
| 126 | H | —CO—C₃H₇-i | H | CH₃ | 4-cyclopropyl-2-methyl-5-trifluoromethyl-2,4-dihydro-3H-1,2,4-triazol-3-one | 139 |

TABLE 1a-continued

Examples of the compounds of the formula (Ia)

| Ex No. | R¹ | R² | R³ | R⁴ | Z | Melting point (° C.) |
|---|---|---|---|---|---|---|
| 127 | H | —CO—C$_3$H$_7$-i | H | H | 4-methyl-1-methyl-3-trifluoromethyl-1,2,4-triazol-5(4H)-one | 114 |
| 128 | H | —CO—OCH$_3$ | H | H | 4-methyl-1-methyl-3-trifluoromethyl-1,2,4-triazol-5(4H)-one | (amorphous) |
| 129 | H | —CO—OCH$_3$ | H | CH$_3$ | 4-cyclopropyl-1-methyl-3-trifluoromethyl-1,2,4-triazol-5(4H)-one | (amorphous) |
| 130 | H | —CO—OCH$_3$ | H | CH$_3$ | 4-methyl-1-methyl-3-trifluoromethyl-1,2,4-triazol-5(4H)-one | 109 |
| 131 | H | —CO—OCH$_3$ | Cl | H | 2-methyl-6,7-dihydro-5H-pyrrolo[2,1-c][1,2,4]triazol-3(2H)-one | 141 |
| 132 | H | —CO—OCH$_3$ | Cl | H | 2-methyl-6,7,8,8a-tetrahydro-[1,2,4]triazolo[4,3-a]pyridin-3(2H)-one | 111 |
| 133 | H | —CO—OCH$_3$ | Cl | H | 2-methyl-6,7,8,9-tetrahydro-[1,2,4]triazolo[4,3-a]azepin-3(2H)-one | 120 |
| 134 | H | —CO—OCH$_3$ | Cl | H | 1,4-dimethyl-3-methyl-1,2,4-triazol-5(4H)-one | 141 |

TABLE 1a-continued
Examples of the compounds of the formula (Ia)
| Ex No. | R¹ | R² | R³ | R⁴ | Z | Melting point (° C.) |
|---|---|---|---|---|---|---|
| 135 | H | —CO—OCH₃ | Cl | H | 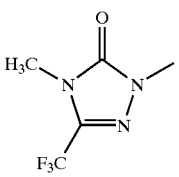 | 105 |
| 136 | H | 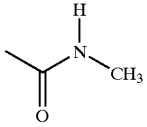 | Cl | H | 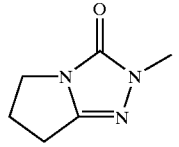 | 188 |
| 137 | H | 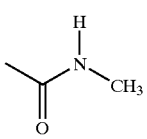 | Cl | H | 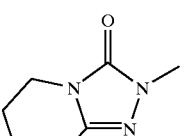 | 185 |
| 138 | H | 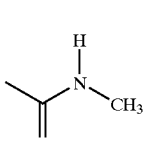 | Cl | H | 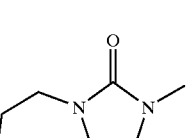 | 240 |
| 139 | H | 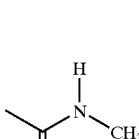 | Cl | H | 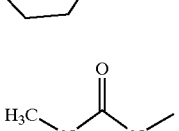 | 210 |
| 140 | H | 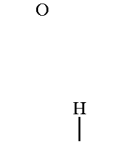 | Cl | H | 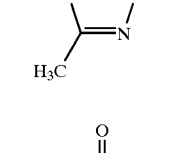 | 154 |
| 141 | H | —CO—OCH₃ | H | H | 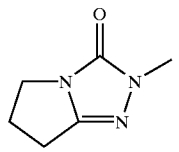 | (amorphous) |
| 142 | H | —CO—OCH₃ | H | H | 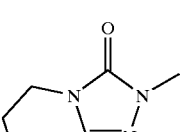 | (amorphous) |

TABLE 1a-continued
Examples of the compounds of the formula (Ia)
| Ex No. | R¹ | R² | R³ | R⁴ | Z | Melting point (° C.) |
|---|---|---|---|---|---|---|
| 143 | H | —CO—OCH₃ | H | H | 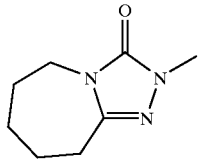 | (amorphous) |
| 144 | H | 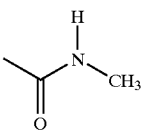 | H | H | 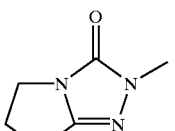 | (amorphous) |
| 145 | H | 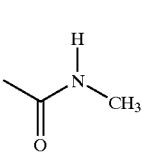 | H | H | 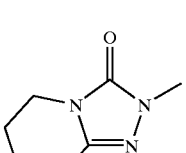 | 189 |
| 146 | H | 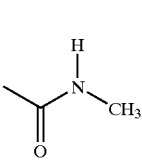 | H | H | 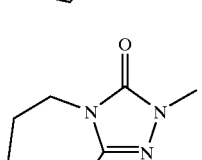 | 154 |
| 147 | 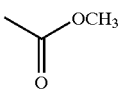 | 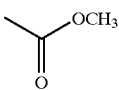 | Cl | H | 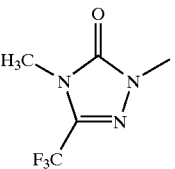 | 175 |
| 148 | H | 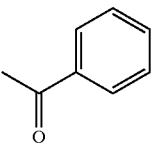 | Cl | H | 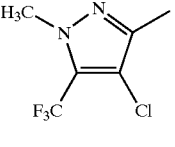 | 160 |
| 149 | H | 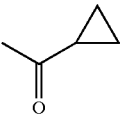 | Cl | H | 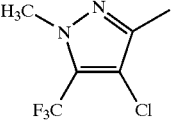 | 71 |
| 150 | H | 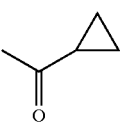 | Cl | H | 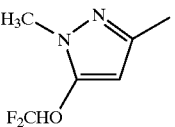 | 121 |
| 151 | H | 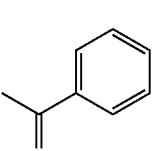 | Cl | H | 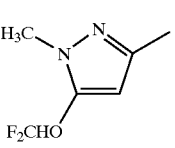 | 99 |

TABLE 1a-continued

Examples of the compounds of the formula (Ia)

| Ex No. | $R^1$ | $R^2$ | $R^3$ | $R^4$ | Z | Melting point (° C.) |
|---|---|---|---|---|---|---|
| 152 | H | cyclopropyl-C(O)- | Cl | H | 1-methyl-3-methyl-4-chloro-5-(OCHF$_2$)-pyrazole | 71 |
| 153 | H | phenyl-C(O)- | Cl | H | 1-methyl-3-methyl-4-chloro-5-(OCHF$_2$)-pyrazole | 115 |
| 154 | H | cyclopropyl-C(O)- | Cl | H | 1-methyl-3-methyl-5-CF$_3$-pyrazole | 114 |
| 155 | H | phenyl-C(O)- | Cl | H | 1-methyl-3-methyl-5-CF$_3$-pyrazole | 132 |
| 156 | H | cyclopropyl-C(O)- | H | H | 1-methyl-3-methyl-5-CF$_3$-pyrazole | 87 |
| 157 | H | phenyl-C(O)- | H | H | 1-methyl-3-methyl-5-CF$_3$-pyrazole | 128 |
| 158 | H | cyclopropyl-C(O)- | H | H | 1-methyl-3-methyl-4-Cl-5-CF$_3$-pyrazole | 104 |
| 159 | H | phenyl-C(O)- | H | H | 1-methyl-3-methyl-4-Cl-5-CF$_3$-pyrazole | 129 |

Another subgroup of the active compounds according to the invention may be represented by the general formula (Ib) below:

(Ib)

TABLE 1b

Examples of the compounds of the formula (Ib)

| Ex. No. | R¹ | R² | R³ | R⁴ | Z | Melting point (° C.) |
|---|---|---|---|---|---|---|
| 160 | H | —CO—CH₃ | H | Cl | (triazolidinedione with N-CH₃, N-CH₃, N-cyclopropyl) | 147 |
| 161 | H | —CO—cyclopropyl | H | Cl | (triazolidinedione with N-CH₃, N-CH₃, N-cyclopropyl) | 66 |
| 162 | H | —CO—C₂H₅ | H | Cl | (triazolidinedione with N-CH₃, N-CH₃, N-cyclopropyl) | 148 |
| 163 | H | —CO—C₃H₇-i | H | Cl | (triazolidinedione with N-CH₃, N-CH₃, N-cyclopropyl) | 176 |
| 164 | H | —C(O)—N(H)—C₂H₅ | H | Cl | (triazolidinedione with N-CH₃, N-CH₃, N-cyclopropyl) | 120 |
| 165 | H | —CO—CH₃ | H | Cl | (triazolidinedione with N-CH₃, N-CH₃, N-(4-chlorophenyl)) | 118 |

TABLE 1b-continued

Examples of the compounds of the formula (Ib)

| Ex. No. | R¹ | R² | R³ | R⁴ | Z | Melting point (° C.) |
|---|---|---|---|---|---|---|
| 166 | H | —CO—C₂H₅ | H | Cl | (1,2-dimethyl-4-(4-chlorophenyl)-1,2,4-triazolidine-3,5-dione) | 84 |
| 167 | H | —CO—C₃H₇-i | H | Cl | (1,2-dimethyl-4-(4-chlorophenyl)-1,2,4-triazolidine-3,5-dione) | 86 |
| 168 | H | —CO-cyclopropyl | H | Cl | (1,2-dimethyl-4-(4-chlorophenyl)-1,2,4-triazolidine-3,5-dione) | 110 |

TABLE 1c

Examples of the compounds of the formula (Ia)

| Ex. No. | R¹ | R² | R³ | R⁴ | Z | Melting point (° C.) |
|---|---|---|---|---|---|---|
| 169 | H | —CO-cyclopropyl | H | CH₃ | (6-trifluoromethyl-1-methyl-pyrimidin-2(1H)-one) | (amorphous) |
| 170 | H | —CO-(4-F-C₆H₄) | H | CH₃ | (6-trifluoromethyl-1-methyl-pyrimidin-2(1H)-one) | 215 |
| 171 | —CO-(4-F-C₆H₄) | —CO-(4-F-C₆H₄) | Cl | H | (6-cyano-1,3-dimethyl-pyrimidine-2,4(1H,3H)-dione) | 260 |
| 172 | H | —CO—CH₃ | Cl | H | (6-cyano-1,3-dimethyl-pyrimidine-2,4(1H,3H)-dione) | 212 |

TABLE 1c-continued

Examples of the compounds of the formula (Ia)

| Ex. No. | R¹ | R² | R³ | R⁴ | Z | Melting point (° C.) |
|---|---|---|---|---|---|---|
| 173 | H | -C(=O)-C(CH₃)₃ | Cl | H | 1,3-dimethyl-6-cyano-uracil-5-yl | 221 |
| 174 | H | -C(=O)-C₆H₅ | Cl | H | 1,3-dimethyl-6-cyano-uracil-5-yl | 208 |
| 175 | H | -C(=O)-(3-F-C₆H₄) | Cl | H | 1,3-dimethyl-6-cyano-uracil-5-yl | 215 |
| 176 | H | -C(=O)-NHC₂H₅ | CF₃ | H | 1,4-dimethyl-1,2,4-triazolidine-3,5-dione-2-yl | 194 |
| 177 | H | -C(=O)-NHCH₃ | Cl | H | 2-methyl-6,7-dihydro-5H-[1,2,4]triazolo[3,4-b][1,3]oxazin-3(2H)-one | 199 |
| 178 | H | -C(=O)-OCH₃ | Cl | H | 2-methyl-6,7-dihydro-5H-[1,2,4]triazolo[3,4-b][1,3]oxazin-3(2H)-one | 153 |
| 179 | H | -C(=O)-C₃H₇-i | Cl | H | 2-methyl-6,7-dihydro-5H-[1,2,4]triazolo[3,4-b][1,3]oxazin-3(2H)-one | 178 |
| 180 | H | -C(=O)-cyclopropyl | Cl | H | 2-methyl-6,7-dihydro-5H-[1,2,4]triazolo[3,4-b][1,3]oxazin-3(2H)-one | 201 |

TABLE 1c-continued

Examples of the compounds of the formula (Ia)

| Ex. No. | R¹ | R² | R³ | R⁴ | Z | Melting point (° C.) |
|---|---|---|---|---|---|---|
| 181 | H | C(O)-phenyl | Cl | H | 5,6-dihydro-2-methyl-[1,2,4]triazolo[3,4-b][1,3]oxazin-3(2H)-one | 179 |
| 182 | H | C(O)-iC₃H₇ | Cl | H | 2,4-dimethyl-5-trifluoromethyl-2,4-dihydro-[1,2,4]triazol-3-one | 108 |
| 183 | H | C(O)-cyclopropyl | Cl | H | 2,4-dimethyl-5-trifluoromethyl-2,4-dihydro-[1,2,4]triazol-3-one | 113 |
| 184 | H | C(O)-phenyl | Cl | H | 2,4-dimethyl-5-trifluoromethyl-2,4-dihydro-[1,2,4]triazol-3-one | 153 |
| 185 | H | C(O)-iC₃H₇ | Cl | H | 2-methyl-6,7,8,8a-tetrahydro-[1,2,4]triazolo[4,3-a]pyridin-3(2H)-one | 99 |
| 186 | H | C(O)-cyclopropyl | Cl | H | 2-methyl-6,7,8,8a-tetrahydro-[1,2,4]triazolo[4,3-a]pyridin-3(2H)-one | 147 |
| 187 | H | C(O)-phenyl | Cl | H | 2-methyl-6,7,8,8a-tetrahydro-[1,2,4]triazolo[4,3-a]pyridin-3(2H)-one | 191 |
| 188 | H | C(O)-iC₃H₇ | Cl | H | 4-chloro-5-difluoromethoxy-1,3-dimethylpyrazole | 85 |
| 189 | H | C(O)-2-furyl | Cl | H | 4-chloro-5-difluoromethoxy-1,3-dimethylpyrazole | 163 |

TABLE 1c-continued
Examples of the compounds of the formula (Ia)
| Ex. No. | R¹ | R² | R³ | R⁴ | Z | Melting point (° C.) |
|---|---|---|---|---|---|---|
| 190 | H | 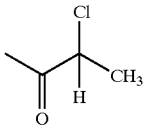 | Cl | H | 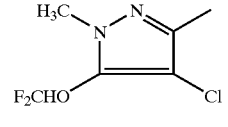 | 99 |
| 191 | H | 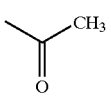 | Cl | H | 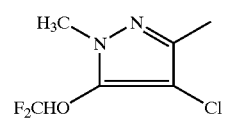 | 137 |
| 192 | H | 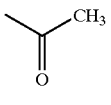 | Cl | H | 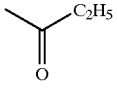 | 120 |
| 193 | H | 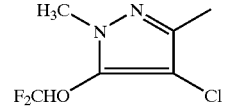 | Cl | H | 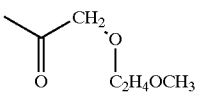 | 58 |
| 194 | H | 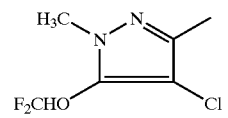 | Cl | H | 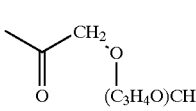 | 40 |
| 195 | H | 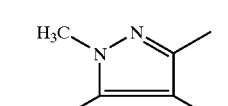 | Cl | H | 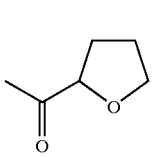 | 125 |
| 196 | H | 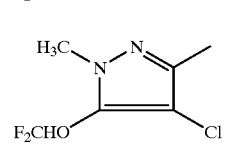 | Cl | H | 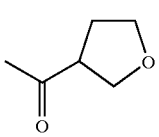 | 86 |
| 197 | H | 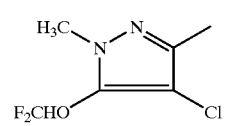 | Cl | H | 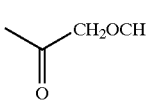 | 174 |
| 198 | H | 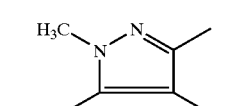 | Cl | H | 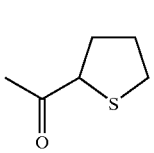 | 129 |
| 199 | H | 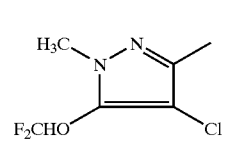 | F | H | 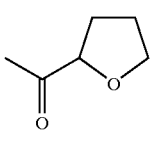 | 100 |

TABLE 1c-continued
Examples of the compounds of the formula (Ia)
| Ex. No. | R¹ | R² | R³ | R⁴ | Z | Melting point (° C.) |
|---|---|---|---|---|---|---|
| 200 | H | 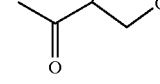 | F | H | 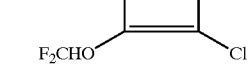 | 55 |
| 201 | H | 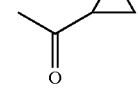 | F | H | 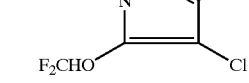 | 98 |
| 202 | H | 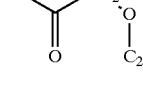 | F | H | 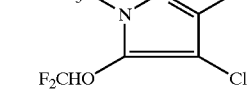 | 58 |
| 203 | H | 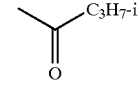 | F | H | 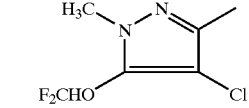 | 63 |
| 204 | H | 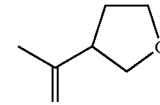 | Br | H | 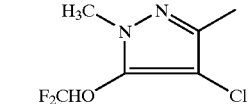 | (amorphous) |
| 205 | H | 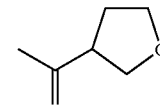 | CN | H | 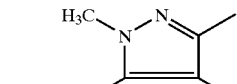 | (amorphous) |
| 206 | H | 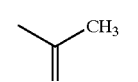 | Cl | H | 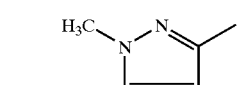 | (amorphous) |
| 207 | H | 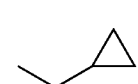 | Cl | H | 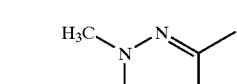 | (amorphous) |
| 208 | H | 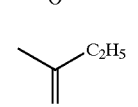 | Cl | H | 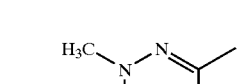 | (amorphous) |
| 209 | H | 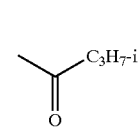 | Cl | H | 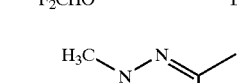 | (amorphous) |
| 210 | H |  | Cl | H | 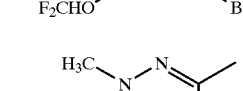 | (amorphous) |

TABLE 1c-continued

Examples of the compounds of the formula (Ia)

| Ex. No. | R¹ | R² | R³ | R⁴ | Z | Melting point (° C.) |
|---|---|---|---|---|---|---|
| 211 | H | -C(=O)-CH₃ | Cl | H | 1-CH₃, 3-CH₃, 4-Cl, 5-SCH₃ pyrazol-yl | (amorphous) |
| 212 | H | -C(=O)-H | Cl | H | 1-CH₃, 3-CH₃, 4-Br, 5-OCHF₂ pyrazol-yl | (amorphous) |
| 213 | H | -C(=O)-NHCH₃ | Cl | H | 1-CH₃, 3-CH₃, 4-Br, 5-OCHF₂ pyrazol-yl | (amorphous) |
| 214 | H | -C(=O)-CH₃ | Cl | H | 1-CH₃, 3-CH₃, 4-Br, 5-SCH₃ pyrazol-yl | (amorphous) |
| 215 | H | -C(=O)-cyclopropyl | Cl | H | 1-CH₃, 3-CH₃, 4-Cl, 5-SCH₃ pyrazol-yl | (amorphous) |
| 216 | H | -C(=O)-cyclopropyl | Cl | H | 1-CH₃, 3-CH₃, 4-Br, 5-SCH₃ pyrazol-yl | (amorphous) |
| 217 | H | -C(=O)-CH₃ | Cl | H | 1-CH₃, 3-CH₃, 4-Cl, 5-SO₂CH₃ pyrazol-yl | (amorphous) |
| 218 | H | -C(=O)-CH₃ | Cl | H | 1-CH₃, 3-CH₃, 4-Br, 5-SO₂CH₃ pyrazol-yl | (amorphous) |
| 219 | H | -C(=O)-cyclopropyl | Cl | H | 1-CH₃, 3-CH₃, 4-Cl, 5-SO₂CH₃ pyrazol-yl | (amorphous) |
| 220 | H | -C(=O)-cyclopropyl | Cl | H | 1-CH₃, 3-CH₃, 4-Br, 5-SO₂CH₃ pyrazol-yl | (amorphous) |

TABLE 1c-continued

Examples of the compounds of the formula (Ia)

| Ex. No. | R¹ | R² | R³ | R⁴ | Z | Melting point (° C.) |
|---|---|---|---|---|---|---|
| 221 | H | 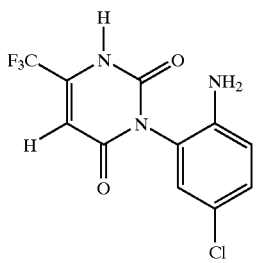 | Cl | H | 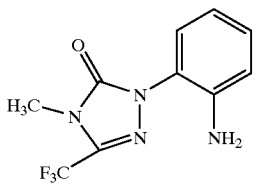 | (amorphous) |

Starting Materials of the Formula (II):

Example (II-1)

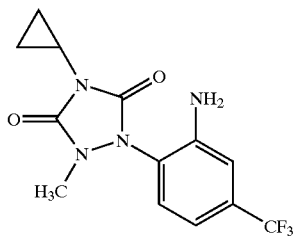

A mixture of 15.0 g (44.7 mmol) of 1-(5-chloro-2-nitro-phenyl)-3,6-dihydro-2,6-dioxo-4-trifluoromethyl-1(2H)-pyrimidine, 30.25 g of tin(II) chloride dihydrate, 20 ml of water and 100 ml of 33% strength hydrochloric acid is stirred for 45 minutes at 80° C. and subsequently concentrated under a water pump vacuum. The residue is then taken up in water and poured into a 5% strength aqueous solution of sodium dihydrogenphosphate and into ethyl acetate. The organic phase is separated off, washed with 5% strength aqueous solution of sodium dihydrogenphosphate, dried with sodium sulphate and filtered. The filtrate is concentrated under a water pump vacuum, the residue is digested with diethyl ether/petroleum ether and the product, which is obtained as crystals, is isolated by filtration with suction.

This gives 11.6 g (85% of theory) of 1-(2-amino-5-chloro-phenyl)-3,6-dihydro-2,6-dioxo-4-trifluoromethyl-1(2H)-pyrimidine of melting point 293° C.

Example (II-2)

A mixture of 2.3 g (7 mmol) of 1-(2-nitro-4-trifluoromethyl-phenyl)-5-cyclopropyl-2-methyl-3,5-dioxo-1,2,4-triazole, 2.4 g (42 mmol) of iron and 100 ml of 50% strength aqueous ethanol is refluxed, during which process a solution of 0.2 ml of concentrated hydrochloric acid in 10 ml of 50% strength aqueous ethanol is added dropwise to the mixture. The reaction mixture is refluxed for 60 minutes and then filtered by suction through silica gel. The solvent is carefully removed from the filtrate by distillation under a water pump vacuum.

This gives 2.4 g (98% of theory) of 1-(2-amino-4-trifluoromethyl-phenyl)-5-cyclopropyl-2-methyl-3,5-dioxo-1,2,4-triazole as crystalline residue of melting point 154° C.

Example (II-3)

12 g (41 mmol) of 4-methyl-2-(2-nitro-phenyl)-5-trifluoromethyl-2,4-dihydro-3H-1,2,4-triazol-3-one are dissolved in 100 ml of methanol and hydrogenated for 4 hours at 50° C. and a hydrogen pressure of 50 bar in the presence of 3 g of Raney nickel. When cold, the batch is filtered and the filtrate is concentrated under a water pump vacuum. The residue is then dried azeotropically with toluene. After reconcentration, the residue is digested with petroleum ether, and the product, which is obtained as crystals, is isolated by filtration with suction.

This gives 10 g (94% of theory) of 2-(2-amino-phenyl)-4-methyl-5-trifluoromethyl-2,4-dihydro-3H-1,2,4-triazol-3-one of melting point 101° C.

Other examples of the compounds of the formula (II) which can be prepared analogously to preparation examples (II-1) to (II-3) are those given in Tables (2a and 2b) which follow.

(II)

Many of the precursors according to the invention can be represented by the general formula (IIa) which follows:

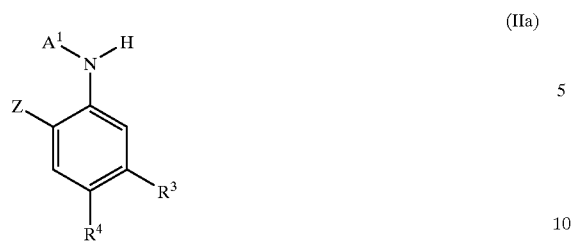

(IIa)

TABLE 2a

Examples of the compounds of the formula (IIa)

| Ex. No. | A¹ | R³ | R⁴ | Z | Melting point (° C.) |
|---|---|---|---|---|---|
| II-4 | H | H | H | 6-(trifluoromethyl)-3-methyl-4(3H)-pyrimidinone | (amorphous) |
| II-5 | H | Cl | H | 6-(trifluoromethyl)-3-methyl-4(3H)-pyrimidinone | 197 |
| II-6 | H | Cl | H | 6-(trifluoromethyl)-3-methyl-2,4(1H,3H)-pyrimidinedione | 295 |
| II-7 | H | CH₃ | H | 6-(trifluoromethyl)-3-methyl-2,4(1H,3H)-pyrimidinedione | 315 |
| II-8 | H | H | H | 6-(trifluoromethyl)-3-methyl-2,4(1H,3H)-pyrimidinedione | 316 |
| II-9 | H | F | H | 6-(trifluoromethyl)-3-methyl-2,4(1H,3H)-pyrimidinedione | 212 |

TABLE 2a-continued
Examples of the compounds of the formula (IIa)
| Ex. No. | A¹ | R³ | R⁴ | Z | Melting point (° C.) |
|---|---|---|---|---|---|
| II-10 | H | OCH₃ | H | 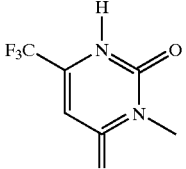 | >300 |
| II-11 | H | Cl | H | 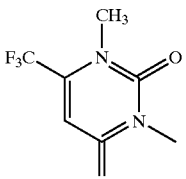 | 166 |
| II-12 | H | NO₂ | H | 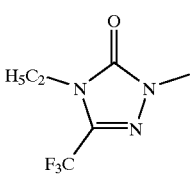 | 148 |
| II-13 | H | NO₂ | H | 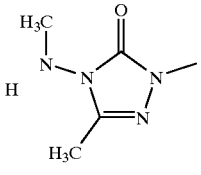 | 152 |
| II-14 | H | H | H | 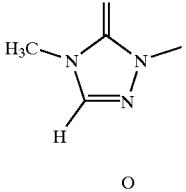 | 232 |
| II-15 | H | H | H | 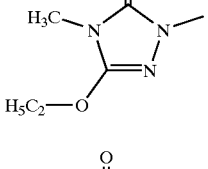 | 162 |
| II-16 | H | H | H | 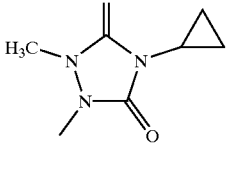 | 140 |
| II-17 | H | H | H | 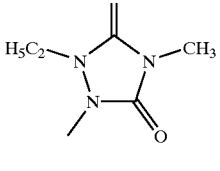 | (amorphous) |

TABLE 2a-continued

Examples of the compounds of the formula (IIa)

| Ex. No. | A¹ | R³ | R⁴ | Z | Melting point (° C.) |
|---|---|---|---|---|---|
| II-18 | CH₃ | H | H | (structure) | 122 |
| II-19 | H | H | H | (structure) | 160 |
| II-20 | H | H | H | (structure) | 120 |
| II-21 | H | H | H | (structure) | 78 |
| II-22 | H | Cl | H | (structure) | 120 |
| II-23 | H | H | H | (structure) | 210 |
| II-24 | H | H | CH₃ | (structure) | (amorphous) |
| II-25 | H | H | H | (structure) | 89 |

TABLE 2a-continued

Examples of the compounds of the formula (IIa)

| Ex. No. | A¹ | R³ | R⁴ | Z | Melting point (° C.) |
|---------|----|----|----|---|---------------------|
| II-26 | H | F | H | 1,2-dimethyl-1,2,4-triazolidine-3,5-dione (NH) | 225 |
| II-27 | H | F | H | 2,4-dimethyl-1,2,4-triazine-3,5-dione | 192 |
| II-28 | H | H | CH₃ | 4-cyclopropyl-2-methyl-5-(trifluoromethyl)-2,4-dihydro-3H-1,2,4-triazol-3-one | 99 |
| II-29 | H | H | CH₃ | 2,4-dimethyl-5-(trifluoromethyl)-2,4-dihydro-3H-1,2,4-triazol-3-one | 115 |
| II-30 | H | Cl | H | 2-methyl-6,7-dihydro-5H-pyrrolo[2,1-c][1,2,4]triazol-3(2H)-one | 114 |
| II-31 | H | Cl | H | 2-methyl-5,6,7,8-tetrahydro-[1,2,4]triazolo[4,3-a]pyridin-3(2H)-one | 178 |
| II-32 | H | Cl | H | 2-methyl-6,7,8,9-tetrahydro-5H-[1,2,4]triazolo[4,3-a]azepin-3(2H)-one | 130 |
| II-33 | H | Cl | H | 2,4,5-trimethyl-2,4-dihydro-3H-1,2,4-triazol-3-one | 148 |

TABLE 2a-continued
Examples of the compounds of the formula (IIa)
| Ex. No. | A¹ | R³ | R⁴ | Z | Melting point (° C.) |
|---|---|---|---|---|---|
| II-34 | H | Cl | H | 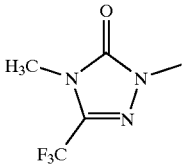 | 141 |
| II-35 | H | H | H | 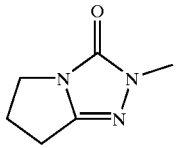 | 159 |
| II-36 | H | H | H | 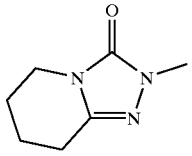 | 187 |
| II-37 | H | Cl | H | 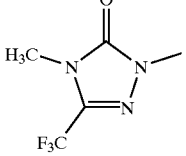 | (amorphous) |
| II-38 | H | Cl | H | 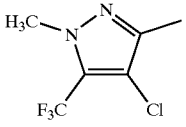 | 40 |
| II-39 | H | Cl | H | 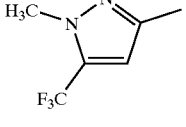 | (amorphous) |
| II-40 | H | Cl | H | 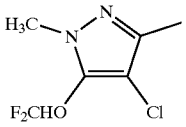 | (amorphous) |
| II-41 | H | H | H | 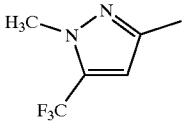 | 132 |
| II-42 | H | H | H | 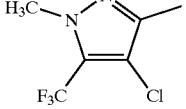 | (amorphous) |

Another subgroup of the precursors according to the invention may be represented by the general formula (IIb) below:

(IIb)

TABLE 2b

Examples of the compounds of the formula (IIb)

| Example No. | A¹ | R³ | R⁴ | Z | Melting point (° C.) |
|---|---|---|---|---|---|
| II-43 | H | H | Cl | (1-methyl-3-methyl-5-oxo-4-cyclopropyl-1,2,4-triazol-3(2H)-one) | 177 |
| II-44 | H | Cl | H | (1-methyl-3-methyl-5-oxo-4-cyclopropyl-1,2,4-triazol-3(2H)-one) | 140 |
| II-45 | H | H | Cl | (1-methyl-3-methyl-5-oxo-4-(4-chlorophenyl)-1,2,4-triazol-3(2H)-one) | 167 |
| II-46 | H | Cl | H | (6-cyano-1,3-dimethyl-pyrimidine-2,4-dione) | 94 |
| II-47 | H | CF₃ | H | (4-isopropyl-2-methyl-1,2,4-triazolidine-3,5-dione) | 137 |
| II-48 | H | CF₃ | H | (4-tert-butyl-2-methyl-1,2,4-triazolidine-3,5-dione) | 194 |

TABLE 2b-continued

Examples of the compounds of the formula (IIb)

| Example No. | A¹ | R³ | R⁴ | Z | Melting point (° C.) |
|---|---|---|---|---|---|
| II-49 | H | CF₃ | H | (triazolidinedione structure with H-N, N-CH₃, N-CH₃, two C=O) | 173 |
| II-50 | H | Cl | H | (bicyclic oxazine-triazolone structure with N-CH₃, C=O) | 168 |
| II-51 | H | F | H | H₃C-N-N=, F₂CHO, Cl, CH₃ (pyrazole) | 62 |
| II-52 | H | CN | H | H₃C-N-N=, F₂CHO, Cl, CH₃ (pyrazole) | (amorphous) |
| II-53 | H | Cl | H | H₃C-N-N=, F₂CHO, Br, CH₃ (pyrazole) | (amorphous) |
| II-54 | H | Cl | H | H₃C-N-N=, H₃CS, Cl, CH₃ (pyrazole) | (amorphous) |
| II-55 | H | Cl | H | H₃C-N-N=, H₃CS, Br, CH₃ (pyrazole) | (amorphous) |

Starting Materials of the Formula (IV)

Example (IV-1)

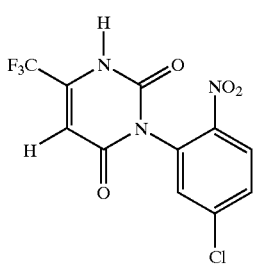

Step 1

118.9 g (109.5 mmol) of 5-chloro-2-nitro-aniline are dissolved in 150 ml of acetone, and 27 g (128 mmol) of trichloromethyl chloroformate ("diphosgene") are added dropwise with stirring to this solution at room temperature (approx. 20° C). The reaction mixture is stirred for 30 minutes, and 150 ml of ethanol are then added dropwise. After a further 30 minutes, the mixture is concentrated under a water pump vacuum, the residue is digested with water/petroleum ether, and the product, which is obtained as crystals, is isolated by filtration with suction.

This gives 22.4 g (84% of theory) of N-(5-chloro-2-nitrophenyl)-O-ethyl-urethane of melting point 86° C.

Step 2

25 g (0.10 mol) of ethyl 3-amino-4,4,4-trifluoro-crotonate are introduced into 100 ml of N,N-dimethyl-formamide. After 3.5 g (0.15 mol) of sodium hydride have been added, the mixture is stirred for 30 minutes at room temperature (approx. 20° C.), and 24.5 g (0.10 mol) of N-(5-chloro-2-nitro-phenyl)-O-ethyl-urethane (cf. Step 1) are then added. The reaction mixture is then heated for 150 minutes at 130° C. and subsequently poured into approximately the same volume of ice-water. The mixture is shaken twice with ethyl acetate, the aqueous phase is then acidified with 2 N hydrochloric acid, and the mixture is shaken again with ethyl acetate. The organic phase is washed with water, dried with sodium sulphate and filtered. The filtrate is concentrated under a water pump vacuum, the residue is digested with 5 ml of ethyl acetate, 50 ml of diethyl ether and 50 ml of petroleum ether, and the product, which is obtained as crystals, is isolated by filtration with suction.

This gives 21 g (62.5% of theory) of 1-(5-chloro-2-nitrophenyl)-3,6-dihydro-2,6-dioxo-4-trifluoromethyl-1(2H)-pyrimidine of melting point 214° C.

Example (IV-2)

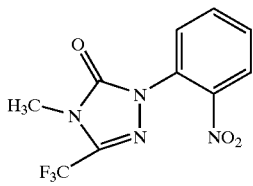

8.4 g (0.05 mol) of 4-methyl-5-trifluoromethyl-2,4-dihydro-3H-1,2,4-triazol-3-one are dissolved in 50 ml of dimethyl sulphoxide, and 6.9 g (0.05 mol) of potassium carbonate (powder) and 7.0 g (0.05 mol) of 2-fluoronitrobenzene are added. The reaction mixture is then heated for 16 hours at 80° C., with stirring, and, when cold, poured into 200 ml of water. The mixture is extracted twice with methylene chloride, the combined organic phases are washed with water, dried with magnesium sulphate and filtered. The filtrate is concentrated under a water pump vacuum, the residue is digested with diethyl ether, and the product, which is obtained as crystals, is isolated by filtration with suction.

This gives 12.7 g (88% of theory) of 4-methyl-2-(2-nitrophenyl)-5-trifluoromethyl-2,4-dihydro-3H-1,2,4-triazol-3-one of melting point 83° C.

Other examples of the compounds of the formula (IV) which can be prepared analogously to preparation examples (IV-1) and (IV-2) are those given in Tables (3a and 3b) which follow.

(IV)

Many of the precursors according to the invention can be represented by the general formula (IVa) below:

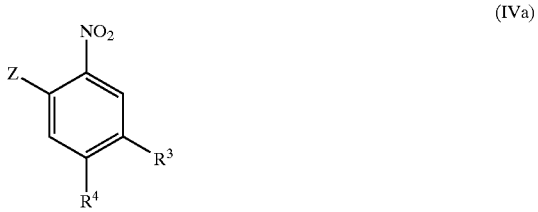

(IVa)

TABLE 3a

Examples of the compounds of the formula (IVa)

| Ex. No. | R³ | R⁴ | Z | Melting point (° C.) |
|---|---|---|---|---|
| IV-3 | Cl | H | F₃C-pyrimidinone-N-CH₃ | 124 |
| IV-4 | H | H | F₃C-pyrimidinone-N-CH₃ | 113 |
| IV-5 | H | CH₃ | F₃C-pyrimidinone-N-CH₃ | (amorphous) |
| IV-6 | H | Cl | CN-triazinedione (H₃C-N, N-CH₃) | 200 |

TABLE 3a-continued

Examples of the compounds of the formula (IVa)

| Ex. No. | R³ | R⁴ | Z | Melting point (° C.) |
|---|---|---|---|---|
| IV-7 | H | Cl | 6-CF₃, N1-CH₃, N3-CH₃ pyrimidine-2,4-dione | 144 |
| IV-8 | Cl | H | 6-CF₃, N1-H, N3-CH₃ pyrimidine-2,4-dione | 215 |
| IV-9 | Cl | H | 6-CF₃, N1-CH₃, N3-CH₃ pyrimidine-2,4-dione | 180 |
| IV-10 | CH₃ | H | 6-CF₃, N1-H, N3-CH₃ pyrimidine-2,4-dione | 250 |
| IV-11 | CH₃ | H | 6-CF₃, N1-CH₃, N3-CH₃ pyrimidine-2,4-dione | 171 |
| IV-12 | H | H | 6-CF₃, N1-H, N3-CH₃ pyrimidine-2,4-dione | 215 |
| IV-13 | H | H | 6-CF₃, N1-CH₃, N3-CH₃ pyrimidine-2,4-dione | 108 |

TABLE 3a-continued

Examples of the compounds of the formula (IVa)

| Ex. No. | R³ | R⁴ | Z | Melting point (° C.) |
|---------|-----|-----|---|----------------------|
| IV-14 | CF₃ | H | 1,3-dimethyl-6-(trifluoromethyl)uracil | 154 |
| IV-15 | F | H | 3-methyl-6-(trifluoromethyl)uracil | 207 |
| IV-16 | F | H | 1,3-dimethyl-6-(trifluoromethyl)uracil | 115 |
| IV-17 | OCH₃ | H | 3-methyl-6-(trifluoromethyl)uracil | 221 |
| IV-18 | OCH₃ | H | 1,3-dimethyl-6-(trifluoromethyl)uracil | 153 |
| IV-19 | H | H | 4-methyl-1,2,4-triazolidine-3,5-dione | 118 |
| IV-20 | H | H | 4-cyclopropyl-1-methyl-1,2,4-triazolidine-3,5-dione | 210 |

TABLE 3a-continued
Examples of the compounds of the formula (IVa)
| Ex. No. | R³ | R⁴ | Z | Melting point (° C.) |
|---|---|---|---|---|
| IV-21 | H | H | 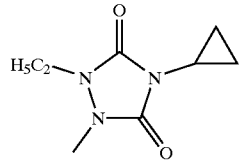 | 136 |
| IV-22 | Cl | H | 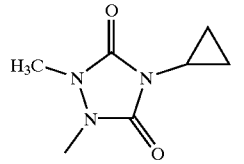 | 87 |
| IV-23 | H | H | 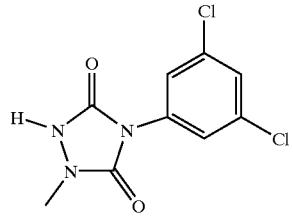 | 213 |
| IV-24 | CF₃ | H | 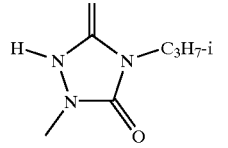 | 100 |
| IV-25 | CF₃ | H | 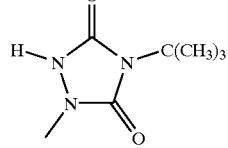 | 115 |
| IV-26 | CF₃ | H | 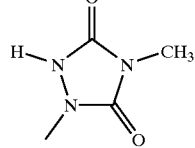 | 138 |
| IV-27 | H | H | 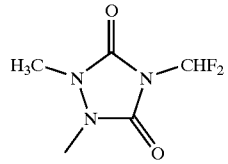 | 98 |
| IV-28 | H | CH₃ | 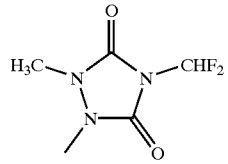 | 119 |

TABLE 3a-continued

Examples of the compounds of the formula (IVa)

| Ex. No. | R³ | R⁴ | Z | Melting point (° C.) |
|---|---|---|---|---|
| IV-29 | H | H | H₃C-N-N(CH₂)₃F triazolidinedione | (amorphous) |
| IV-30 | CF₃ | H | H₃C-N-NH triazolidinedione | 206 |
| IV-31 | NO₂ | H | H₃C-N-NH triazolidinedione | 187 |
| IV-32 | CH₃ | H | H₃C-N-NH triazolidinedione | 222 |
| IV-33 | F | H | H₃C-N-NH triazolidinedione | 204 |
| IV-34 | F | H | H₃C-N-N-CHF₂ triazolidinedione | (amorphous) |
| IV-35 | CF₃ | H | triazinedione (N-methyl) | 160 |
| IV-36 | F | H | triazinedione (N-methyl) | 196 |

TABLE 3a-continued

Examples of the compounds of the formula (IVa)

| Ex. No. | R³ | R⁴ | Z | Melting point (° C.) |
|---|---|---|---|---|
| IV-37 | NH₂ | H | 1,2-dimethyl-1,2,4-triazolidine-3,5-dione (N-H at 4-position) | 253 |
| IV-38 | CH₃ | H | 1,2-dimethyl-4-(CHF₂)-1,2,4-triazolidine-3,5-dione | 107 |
| IV-39 | CF₃ | H | 2,4-dimethyl-1,2,4-triazine-3,5-dione | 94 |
| IV-40 | F | H | 2,4-dimethyl-1,2,4-triazine-3,5-dione | (amorphous) |
| IV-41 | Cl | H | 2-methyl-1,2,4-triazine-3,5-dione (N-H) | 220 |
| IV-42 | Cl | H | 1,2-dimethyl-1,2,4-triazolidine-3,5-dione (N-H at 4-position) | 224 |
| IV-43 | Cl | H | 2,4-dimethyl-1,2,4-triazine-3,5-dione | 52 |
| IV-44 | Cl | H | 1,2-dimethyl-4-(CHF₂)-1,2,4-triazolidine-3,5-dione | 134 |
| IV-45 | H | H | 2,4-dimethyl-5-bromo-1,2,4-triazol-3(2H)-one | 123 |

TABLE 3a-continued

Examples of the compounds of the formula (IVa)

| Ex. No. | $R^3$ | $R^4$ | Z | Melting point (° C.) |
|---|---|---|---|---|
| IV-46 | H | $CH_3$ | 4-methyl-5-bromo-2-methyl-2,4-dihydro-3H-1,2,4-triazol-3-one | 124 |
| IV-47 | H | $CH_3$ | 4-cyclopropyl-5-trifluoromethyl-2-methyl-2,4-dihydro-3H-1,2,4-triazol-3-one | 126 |
| IV-48 | H | $CH_3$ | 4-methyl-5-trifluoromethyl-2-methyl-2,4-dihydro-3H-1,2,4-triazol-3-one | 107 |
| IV-49 | Cl | H | 2-methyl-6,7-dihydro-5H-pyrrolo[2,1-c][1,2,4]triazol-3(2H)-one | 163 |
| IV-50 | Cl | H | 2-methyl-5,6,7,8-tetrahydro-[1,2,4]triazolo[4,3-a]pyridin-3(2H)-one | 157 |
| IV-51 | Cl | H | 2-methyl-6,7,8,9-tetrahydro-5H-[1,2,4]triazolo[4,3-a]azepin-3(2H)-one | 170 |

TABLE 3a-continued

Examples of the compounds of the formula (IVa)

| Ex. No. | R³ | R⁴ | Z | Melting point (° C.) |
|---|---|---|---|---|
| IV-52 | Cl | H | 4,5-dimethyl-3-methyl-1,2,4-triazol-3(4H)-one (H₃C-N, H₃C substituent) | 171 |
| IV-53 | Cl | H | 4-methyl-5-trifluoromethyl-1,2,4-triazol-3(4H)-one (H₃C-N, F₃C substituent) | 94 |
| IV-54 | H | H | 2-methyl-6,7-dihydro-5H-pyrrolo[2,1-c][1,2,4]triazol-3(2H)-one | 128 |
| IV-55 | H | H | 2-methyl-6,7,8,8a-tetrahydro-5H-[1,2,4]triazolo[4,3-a]pyridin-3(2H)-one | 130 |
| IV-56 | H | H | 2-methyl-6,7,8,9-tetrahydro-5H-[1,2,4]triazolo[4,3-a]azepin-3(2H)-one | 112 |
| IV-57 | Cl | H | 1,3-dimethyl-5-(difluoromethoxy)pyrazole | 40 |
| IV-58 | Cl | H | 1,3-dimethyl-4-chloro-5-trifluoromethylpyrazole | 46 |
| IV-59 | H | H | 1,3-dimethyl-4-chloro-5-trifluoromethylpyrazole | (amorphous) |
| IV-60 | Cl | H | 1,3-dimethyl-4-chloro-5-(difluoromethoxy)pyrazole | 64 |

Another subgroup of the precursors according to the invention can be represented by the general formula (IVb) below:

TABLE 3b

Examples of the compounds of the formula (IVb)

| Example No. | R³ | R⁴ | Z | Melting point (° C.) |
|---|---|---|---|---|
| IV-61 | H | Cl | ![structure with H3C-N-N(methyl)-N-cyclopropyl triazolinedione] | 79 |
| IV-62 | H | Cl | ![structure with H3C-N-N(methyl)-N-(4-chlorophenyl) triazolinedione] | 162 |

USE EXAMPLES

Example A
Pre-emergence Test
  Solvent: 5 parts by weight of acetone
  Emulsifier: 1 part by weight of alkylaryl polyglycol ether
  To prepare a suitable preparation of active compound, 1 part by weight of active compound is mixed with the stated amount of solvent, the stated amount of emulsifier is added, and the concentrate is diluted with water to the desired concentration.
  Seeds of the test plants are sown in normal soil. After approx. 24 hours, the soil is sprayed with the preparation of active compound in such a way that the desired amounts of active compound are in each case applied per unit area. The concentration of the spray mixture is chosen in such a way that the desired amounts of active compound are in each case applied in 1,000 liters of water/ha.
  After three weeks, the degree of damage to the plants is scored in % damage in comparison with the development of the untreated control.
  The figures denote:

| | |
|---|---|
| 0% = | no action (like untreated control) |
| 100% = | total destruction |

In this test, for example the compounds of preparation examples 18, 19, 20, 23, 24 and 102 have a potent action against weeds such as Avena fatua (100%), Cyperus (70–100%), Setaria (90–100%), Abutilon (70–100%), Amaranthus (90–100%), Galium (90–100%), Sinapis (95–100%), Lolium (100%), Ipomoea (95–100%), Matricaria (100%) and Solanum (100%) at application rates between 250 and 750 g/ha, while being tolerated well by crop plants such as, for example, wheat (0%).

Example B
Post-emergence Test
  Solvent: 5 parts by weight of acetone
  Emulsifier: 1 part by weight of alkylaryl polyglycol ether
  To prepare a suitable preparation of active compound, 1 part by weight of active compound is mixed with the stated amount of solvent, the stated amount of emulsifier is added, and the concentrate is diluted with water to the desired concentration.
  Test plants which have a height of 5–15 cm are sprayed with the preparation of active compound in such a way that the desired amounts of active compound are in each case applied per unit area. The concentration of the spray mixture is chosen in such a way that the amounts of active compound desired in each case are applied in 1,000 liters of water/ha.
  After three weeks, the degree of damage to the plants is scored in % damage in comparison with the development of the untreated control.
  The figures denote:

| | |
|---|---|
| 0% = | no action (like untreated control) |
| 100% = | total destruction |

In this test, for example the compounds of preparation examples 18, 19, 20, 23, 24 and 102 have a potent action against weeds such as Avena fatua (80–95%), Cyperus (90–95%), Setaria (95–100%), Abutilon (100%), Amaranthus (95–100%), Galium (100%), Sinapis (100%), Chenopodium (95–100%), Matricaria (95–100%), Polygonum (95–100%) and Viola (90–100%) at application rates of 15–750 g/ha, while being tolerated well by crop plants such as, for example, wheat (5–10%).

What is claimed is:

1. An aromatic amino compound of the formula

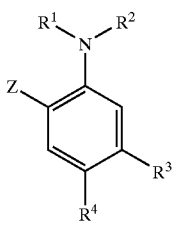

wherein
- $R^1$ represents a moiety selected from the group consisting of hydrogen; hydroxyl; amino; alkyl, alkoxy, alkylamino, or dialkylamino, each of which has 1 to 6 carbon atoms in the alkyl groups; —$CQ^1$—$R^5$; and —$CQ^1$—$Q^2$—$R^6$;
- $R^2$ is selected from the group consisting of —$CQ^1$—$R^5$ and —$CQ^1$—$Q^2$—$R^6$;
- $R^3$ represents a moiety selected from the group consisting of hydrogen; hydroxyl; amino; carboxyl; cyano; carbamoyl; thiocarbamoyl; nitro; halogen; unsubstituted alkyl, alkoxy, alkoxycarbonyl, alkylthio, alkylsulphinyl, or alkylsulphonyl, each of which has 1 to 6 carbon atoms in the alkyl groups; cyano-, halogen-, or $C_1$–$C_4$-alkoxy-substituted alkyl, alkoxy, alkoxycarbonyl, alkylthio, alkylsulphinyl, or alkylsulphonyl, each of which has 1 to 6 carbon atoms in the alkyl groups; —$SO_2$—NH—$R^5$; —NH—$SO_2$—$R^7$; —$N(SO_2$—$R^7)_2$; and —$N(SO_2$—$R^7)(CO$—$R^5)$;
- $R^4$ represents a moiety selected from the group consisting of hydroxyl; amino; carboxyl; cyano; carbamoyl; thiocarbamoyl; nitro; halogen; unsubstituted alkyl, alkoxy, alkoxycarbonyl, alkylthio, alkylsulphinyl, or alkylsulphonyl, each of which has 1 to 6 carbon atoms in the alkyl groups; cyano-, halogen- or $C_1$–$C_4$-alkoxy-substituted alkyl, alkoxy, alkoxycarbonyl, alkylthio, alkyl-sulphinyl, or alkylsulphonyl, each of which has 1 to 6 carbon atoms in the alkyl groups; —$SO_2$—NH—$R^5$; —NH—$SO_2$—$R^7$; —$N(SO_2$—$R^7)_2$; and —$N(SO_2$—$R^7)(CO$—$R^5)$;
- $Q^1$ and $Q^2$ each represent O;
- $R^5$ represents a moiety selected from the group consisting of hydrogen; unsubstituted or cyano-, halogen-, or $C_1$–$C_4$-alkoxy-substituted alkyl which has 1 to 6 carbon atoms; cycloalkyl or cycloalkylalkyl, each of which has 3 to 6 carbon atoms in the cycloalkyl group and, where appropriate, 1 to 4 carbon atoms in the alkyl moiety and each of which is optionally substituted by cyano, halogen, or $C_1$–$C_4$-alkyl; and aryl or arylalkyl, each of which has 6 or 10 carbon atoms in the aryl group and, where appropriate, 1 to 4 carbon atoms in the alkyl moiety and each of which is optionally substituted by cyano, nitro, halogen, $C_1$–$C_4$-alkyl, $C_1$–$C_4$-halogenoalkyl, $C_1$–$C_4$-alkoxy, or $C_1$–$C_4$-halogenoalkoxy;
- $R^6$ represents a moiety selected from the group consisting of alkyl which has 1 to 6 carbon atoms and which is optionally substituted by cyano, halogen, or $C_1$–$C_4$-alkoxy; alkenyl or alkynyl, each of which has 2 to 6 carbon atoms and each of which is optionally substituted by halogen; cycloalkyl or cycloalkylalkyl, each of which has 3 to 6 carbon atoms in the cycloalkyl group and, where appropriate, 1 to 4 carbon atoms in the alkyl moiety and each of which is optionally substituted by cyano, halogen, or $C_1$–$C_4$-alkyl; and aryl or arylalkyl, each of which has 6 or 10 carbon atoms in the aryl group and, where appropriate, 1 to 4 carbon atoms in the alkyl moiety and each of which is optionally substituted by cyano, nitro, halogen, $C_1$–$C_4$-alkyl, $C_1$–$C_4$-halogenoalkyl, $C_1$–$C_4$-alkoxy, or $C_1$–$C_4$-halogenoalkoxy;
- $R^7$ represents a moiety selected from the group consisting of alkyl which has 1 to 6 carbon atoms and which is optionally substituted by halogen; cycloalkyl or cycloalkylalkyl, each of which has 3 to 6 carbon atoms in the cycloalkyl moiety and, where appropriate, 1 to 4 carbon atoms in the alkyl moiety and each of which is optionally substituted by halogen; and aryl or arylalkyl, each of which has 6 or 10 carbon atoms in the aryl group and, where appropriate, 1 to 4 carbon atoms in the alkyl moiety and each of which is optionally substituted by cyano, nitro, halogen, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, $C_1$–$C_4$-alkylsulphinyl, $C_1$–$C_4$-alkyl-sulphonyl, or $C_1$–$C_4$-alkoxy-carbonyl;
- Z represents

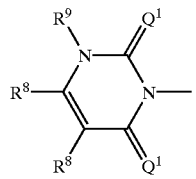

wherein
- $Q^1$ represents O;
- $R^8$ represents a moiety selected from the group consisting of hydrogen; amino; nitro; cyano; carboxyl; carbamoyl; thiocarbamoyl; halogen; alkyl which has 1 to 6 carbon atoms and which is optionally substituted by cyano, halogen or $C_1$–$C_4$-alkoxy; alkenyl or alkynyl, each of which has 2 to 6 carbon atoms and each of which is optionally substituted by halogen; alkoxy or alkoxycarbonyl, each of which has 1 to 6 carbon atoms in the alkyl groups and each of which is optionally substituted by cyano, halogen or $C_1$–$C_4$-alkoxy; alkenyloxy, or alkynyloxy, each of which has 3 to 6 carbon atoms and each of which is optionally substituted by halogen; alkylthio which has 1 to 6 carbon atoms and which is optionally substituted by cyano, halogen, or $C_1$–$C_4$-alkoxy; alkenylthio or alkynylthio, each of which has 3 to 6 carbon atoms and each of which is optionally substituted by halogen; alkylamino or dialkylamino, each of which has 1 to 6 carbon atoms in the alkyl groups, each of which is optionally substituted by cyano, halogen, or $C_1$–$C_4$-alkoxy; and cycloalkyl or cycloalkylalkyl, each of which has 3 to 6 carbon atoms in the cycloalkyl groups and, where appropriate, 1 to 4 carbon atoms in the alkyl moiety and each of which is optionally substituted by cyano, halogen, or $C_1$–$C_4$-alkyl; and $R^9$ represents a moiety selected from the group consisting of hydrogen; hydroxyl; amino; cyano; alkyl which has 1 to 6 carbon atoms and which is optionally substituted by cyano, halogen, or $C_1$–$C_4$-alkoxy; alkenyl or alkynyl, each of which has 2 to 6 carbon atoms and which is optionally substituted by halogen; alkoxycarbonyl, which is optionally substituted by cyano, halogen, or $C_1$–$C_4$-alkoxy; cycloalkyl or cycloalkylalkyl, each of which has 3 to 6 carbon atoms in the cycloalkyl groups and, where appropriate, 1 to 4 carbon atoms in the alkyl moiety and each of which is optionally substituted by cyano, halogen, or $C_1$–$C_4$-alkyl; and phenyl or phenyl-$C_1$–$C_4$-alkyl, each of which is optionally substituted by cyano, nitro, halogen, $C_1$–$C_4$-alkyl, $C_1$–$C_4$-halogenoalkyl, $C_1$–$C_4$-alkoxy and/or $C_1$–$C_4$-halogenoalkoxy, where the individual radicals $R^8$ and $R^9$ may have identical or different meanings.

2. An aromatic amino compound according to claim 1 and having the formula

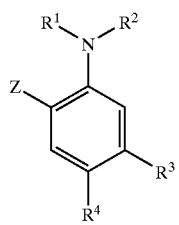

wherein $R^1$ represents a moiety selected from the group consisting of hydrogen; hydroxyl; amino; methyl; ethyl; n- or i-propyl; n-, i-, s-, or t-butyl; methoxy; ethoxy; n- or i-propoxy; n-, i-, s-, or t-butoxy; methylamino; ethylami no; n- or i-propylamino; n-, i-, s-, or t-butylamino or dimethylamino; —$CQ^1$—$R^5$; and —$CQ^1$—$Q^2$—$R^6$;

$R^2$ is selected from the group consisting of —$CQ^1$—$R^5$ and —$CQ^1$—$Q^2$—$R^6$;

$R^3$ represents a moiety selected from the group consisting of hydrogen; hydroxyl; amino; carboxyl; cyano; carbamoyl; thiocarbamoyl; nitro; fluorine; chlorine; bromine; unsubstituted methyl, ethyl, n- or i-propyl, n-, i-, s-, or t-butyl, methoxy, ethoxy, n- or i-propoxy, n-, i-, s-, or t-butoxy, methoxycarbonyl, ethoxycarbonyl, methylthio, ethylthio, n- or i-propylthio, n-, i-, s-, or t-butylthio, methylsulphinyl, ethylsulphinyl, methylsulphonyl, or ethylsulphonyl; cyano-, fluorine-, chlorine-, methoxy-, or ethoxy-substituted methyl, ethyl, n- or i-propyl, n-, i-, s-, or t-butyl, methoxy, ethoxy, n- or i-propoxy, n-, i-, s-, or t-butoxy, methoxycarbonyl, ethoxycarbonyl, methylthio, ethylthio, n- or i-propylthio, n-, i-, s-, or t-butylthio, methylsulphinyl, ethylsulphinyl, methylsulphonyl, or ethylsulphonyl; —$SO_2$—NH—$R^5$; —NH—$SO_2$—$R^7$; —N($SO_2$—$R^7$)$_2$; and —N($SO_2$—$R^7$)(CO—$R^5$);

$R^4$ represents a moiety selected from the group consisting of hydroxyl; amino; carboxyl; cyano; carbamoyl; thiocarbamoyl; nitro; fluorine; chlorine; bromine; unsubstituted methyl, ethyl, n- or i-propyl, n-, i-, s-, or t-butyl, methoxy, ethoxy, n- or i-propoxy, n-, i-, s-, or t-butoxy, methoxycarbonyl, ethoxycarbonyl, methylthio, ethylthio, n- or i-propylthio, n-, i-, s-, or t-butylthio, methylsulphinyl, ethylsulphinyl, methylsulphonyl, or ethylsulphonyl; cyano-, fluorine-, chlorine-, methoxy-, or ethoxy-substituted methyl, ethyl, n- or i-propyl, n-, i-, s-, or t-butyl, methoxy, ethoxy, n- or i-propoxy, n-, i-, s-, or t-butoxy, methoxycarbonyl, ethoxycarbonyl, methylthio, ethylthio, n- or i-propylthio, n-, i-, s-, or t-butylthio, methylsulphinyl, ethylsulphinyl, methylsulphonyl, or ethylsulphonyl; —$SO_2$—NH—$R^5$; —NH—$SO_2$—$R^7$; —N($SO_2$—$R^7$)$_2$; and —N($SO_2$—$R^7$)(CO—$R^5$);

$Q^1$ and $Q^2$ each represent O, $R^5$ represents a moiety selected from the group consisting of hydrogen; unsubstituted methyl, ethyl, n- or i-propyl, n-, i-, s-, or t-butyl; cyano-, fluorine-, chlorine-, bromine-, methoxy-, or ethoxy-substituted methyl, ethyl, n- or i-propyl, n-, i-, s-, or t-butyl; unsubstituted cyclobutyl, cyclopentyl, cyclohexyl, cyclopropylmethyl, cyclobutylmethyl, cyclopentylmethyl or cyclohexylmethyl; and cyano-, fluorine-, chlorine-, bromine-, methyl-, or ethyl-substituted cyclopropyl, cyclobutyl, cyclopentyl, cyclohexyl, cyclopropylmethyl, cyclobutylmethyl, cyclopentylmethyl, or cyclohexylmethyl;

$R^6$ represents a moiety selected from the group consisting of unsubstituted methyl, ethyl, n- or i-propyl, or n-, i-, s-, or t-butyl; cyano-, fluorine-chlorine-, methoxy- or ethoxy-substituted methyl, ethyl, n- or i-propyl, or n-, i-, s-, or t-butyl; unsubstituted propenyl, butenyl, propynyl, or butynyl; fluorine-, chlorine-, or bromine-substituted propenyl, butenyl, propynyl, or butynyl; unsubstituted cyclobutyl, cyclopentyl, cyclohexyl, cyclopropylmethyl, cyclobutylmethyl, cyclopentylmethyl, or cyclohexylmethyl; and cyano-, fluorine-, chlorine-, bromine-, methyl-, or ethyl-substituted cyclopropyl, cyclobutyl, cyclopentyl, cyclohexyl, cyclopropyl methyl, cyclobutylmethyl, cyclopentylmethyl, or cyclohexylmethyl;

$R^7$ represents a moiety selected from the group consisting of unsubstituted methyl, ethyl, n- or i-propyl, or n-, i-, s-, or t-butyl; fluorine-, chlorine- or bromine-substituted methyl, ethyl, n- or i-propyl, or n-, i-, s- or t-butyl; unsubstituted cyclopropyl, cyclobutyl, cyclopentyl, cyclohexyl, cyclopropylmethyl, cyclobutylmethyl, cyclopentylmethyl or cyclohexylmethyl; fluorine-, chlorine- or bromine-substituted cyclopropyl, cyclobutyl, cyclopentyl, cyclohexyl, cyclopropylmethyl, cyclobutylmethyl, cyclopentylmethyl or cyclohexylmethyl; unsubstituted phenyl or benzyl; and cyano-, nitro-, fluorine-, chlorine-, bromine-, methyl-, ethyl-, n- or i-propyl-, n-, i-, s-, or t-butyl-, trifluoromethyl-, methoxy-, ethoxy-, n- or i-propoxy-, n-, i-, s-, or t-butoxy-, difluoromethoxy-, trifluoromethoxy-, methylthio-, ethylthio-, n- or i-propylthio-, n-, i-, s-, or t-butylthio-, methylsulphinyl-, ethylsulphinyl-, methylsulphonyl-, ethylsulphonyl-, methoxycarbonyl-, or ethoxycarbonyl-substituted phenyl or benzyl;

Z represents

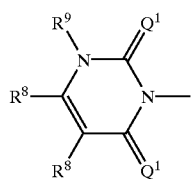

wherein $Q^1$ represents O;

$R^8$ represents a moiety selected from the group consisting of hydrogen; amino; nitro; cyano; carboxyl; carbamoyl; thio-carbamoyl; fluorine; chlorine; bromine; methyl, ethyl, n- or i-propyl, or n-, i-, s-, or t-butyl, each of which is optionally substituted by cyano, fluorine, chlorine, methoxy, or ethoxy; propenyl, butenyl, propynyl, or butynyl, each of which is optionally substituted by fluorine, chlorine, or bromine; methoxy, ethoxy, n- or i-propoxy, n-, i-, s-, or t-butoxy, methoxycarbonyl, or ethoxycarbonyl, each of which is optionally substituted by cyano, fluorine, chlorine, methoxy, or ethoxy; propenyloxy, butenyloxy, propynyloxy, or butynyloxy, each of which is optionally substituted by fluorine or chlorine; methylthio, ethylthio, n- or i-propylthio, or n-, i-, s-, or t-butylthio, each of which is optionally substituted by cyano, fluorine, chlorine, methoxy, or ethoxy; propenylthio, butenylthio, propynylthio, or butynylthio, each of which is optionally substituted by fluorine or chlorine; methylamino, ethylamino, n- or i-propylamino, n-, i-, s-, or t-butylamino, dimethylamino, or diethylamino, each of which is optionally substituted by cyano, fluorine, chlorine, methoxy, or ethoxy; and cyclopropyl, cyclobutyl, cyclopentyl, cyclohexyl, cyclopropylmethyl, cyclobutylmethyl, cyclopentylmethyl, or cyclohexylmethyl, each of which is optionally substituted by cyano, fluorine, chlorine, bromine, methyl, or ethyl; and $R^9$ represents a moiety selected from the group consisting of hydrogen; hydroxyl; amino; cyano; methyl, ethyl, n- or i-propyl, or n-, i-, s-, or t-butyl, each of which is optionally substituted by cyano, fluorine, chlorine, methoxy, or ethoxy; propenyl, butenyl, propynyl, or butynyl, each of which is optionally substituted by fluorine, chlorine, or bromine; methoxycarbonyl, or ethoxycarbonyl, each of which is optionally substituted by cyano, fluorine, chlorine, methoxy, or ethoxy; cyclopropyl, cyclobutyl, cyclopentyl, cyclohexyl, cyclopropylmethyl, cyclobutylmethyl, cyclopentylmethyl, or cyclohexylmethyl, each of which is optionally substituted by cyano, fluorine, chlorine, bromine, methyl, or ethyl; and phenyl or benzyl, each of which is optionally substituted by cyano, nitro, fluorine, chlorine, bromine, methyl, ethyl, n- or i-propyl, n-, i-, s-, or t-butyl, trifluoromethyl, methoxy, ethoxy, n- or i-propoxy, n-, i-, s-, or t-butoxy, difluoromethoxy, and/or trifluoromethoxy, where the individual radicals $R^8$ and $R^9$ may have identical or different meanings.

3. A herbicidal composition comprising one or more aromatic amino compounds of claim 2, and a member selected from the group consisting of surfactants, liquid solvents, solid carriers and mixtures thereof.

4. A method of controlling undesired plants omprising allowing an effective amount of an aromatic amino compound of claim 2 to act on said plants and/or their environment.

* * * * *